US010188721B2

(12) United States Patent
Widener et al.

(10) Patent No.: US 10,188,721 B2
(45) Date of Patent: Jan. 29, 2019

(54) RECOMBINANT ADENOVIRUS VECTORED FMDV VACCINES AND USES THEREOF

(71) Applicants: MERIAL INC., Duluth, GA (US); GENVEC INC., Gaithersburg, MD (US); THE UNITED STATES OF AMERICA, as represented by the Secretary of Homeland Security, Washington, DC (US)

(72) Inventors: Justin Widener, Athens, GA (US); Leszlie Woodyard, Hull, GA (US); Leonardo Siger, Watkinsville, GA (US); Douglas Brough, Gaithersburg, MD (US); Damodar Ettyreddy, Clarksburg, MD (US); Jason Gall, Germantown, MD (US); Duncan McVey, Derwood, MD (US); Tom Burrage, Guilford, CT (US); Lauri Motes-Kreimeyer, Athens, GA (US); Marc Fiorucci, Suwanee, GA (US)

(73) Assignee: Merial, Inc., Duluth, GA (US)

( * ) Notice: Subject to any disclaimer, the term of this patent is extended or adjusted under 35 U.S.C. 154(b) by 0 days.

(21) Appl. No.: 15/419,418

(22) Filed: Jan. 30, 2017

(65) Prior Publication Data
US 2017/0216422 A1 Aug. 3, 2017

Related U.S. Application Data

(60) Provisional application No. 62/288,540, filed on Jan. 29, 2016.

(51) Int. Cl.
*A61K 39/135* (2006.01)
*C07K 14/005* (2006.01)
*C12N 7/00* (2006.01)
*A61K 39/12* (2006.01)
*C12N 15/86* (2006.01)
*A61K 39/00* (2006.01)

(52) U.S. Cl.
CPC .............. *A61K 39/12* (2013.01); *C12N 7/00* (2013.01); *C12N 15/86* (2013.01); *A61K 2039/5256* (2013.01); *A61K 2039/552* (2013.01); *C12N 2710/10034* (2013.01); *C12N 2770/32134* (2013.01); *C12N 2800/107* (2013.01)

(58) Field of Classification Search
None
See application file for complete search history.

(56) References Cited

U.S. PATENT DOCUMENTS

| 7,371,395 | B2 | 5/2008 | Parisot |
| 7,531,182 | B2 | 5/2009 | King |
| 7,608,279 | B2 | 10/2009 | Parisot |
| 7,691,368 | B2 | 4/2010 | Parisot |
| 8,323,663 | B2 | 12/2012 | Brough |
| 2005/0287672 | A1 | 12/2005 | Nordgren et al. |
| 2011/0236416 | A1* | 9/2011 | Audonnet ............... A61K 39/15 424/199.1 |
| 2017/0216422 | A1* | 8/2017 | Widener ................ A61K 39/12 |

FOREIGN PATENT DOCUMENTS

| CA | 2047585 | 1/1992 |
| WO | WO2007/059461 | 5/2007 |
| WO | WO2012/003129 | 1/2012 |

OTHER PUBLICATIONS

Moraes et al. (Vaccine. 2002; 20: 1631-1639).*
Wesley et al. (Veterinary Microbiology. 2006; 118: 67-75).*
EBI accession No. BBG42659.
U.S. Appl. No. 14/863,181, filed Sep. 23, 2015, Audonnet.
Belsham G. J., 1993, "Distinctive features of foot-and-mouth disease virus, a member of the picornavirus family; aspects of virus protein synthesis, protein processing and structure", Progress in Biophysics and Molecular Biology, 60, 241-261.
Brun et al., 1977; Developments in Biological Standardization, 25: 117-122.
Cooper et al., 1978, "Picornaviridae" second report, Intervirology, 10, 165-180.
Graves, 1963, "Transfer of neutralizing antibody by colostrum to calves born of foot-and-mouth disease vaccinated dams", Journal of Immunology 91:251-256.
Grubman et al.,1993, "Protection of swine against foot-and-mouth disease with viral capsid proteins expressed in heterologous systems", Vaccine, 11, 825-829.
Kleid et al. 1981, "Cloned viral protein vaccine for foot-and-mouth disease: responese in cattle and swine", Science, 214, 1125-1129.
Lewis et al., J. Virol., 1991, "Expression, processing, and assembly of foot-and-mouth disease virus capsid structures in heterologous systems: induction of a neutralizing antibody response in guinea pigs", 65, 6572-6580.
Rowlands et al., J., 1975, "A comparative chemical and seroloigical study of the full and empty particles of foot-and-mouth disease virus", Gen. Virol., 26, 227-238.
Rweyemamu et al.,1979, "Stability and immunogenicity of empty particles of foot-and-mouth disease virus", Archives of Virology, 59, 69-79.

* cited by examiner

*Primary Examiner* — Shanon A. Foley
(74) *Attorney, Agent, or Firm* — Judy Jarecki-Black; Suzanne Shope; Merial, Inc.

(57) ABSTRACT

The present invention encompasses FMDV vaccines or compositions. The invention encompasses recombinant vectors encoding and expressing FMDV antigens, epitopes or immunogens which can be used to protect animals, in particular ovines, bovines, caprines, or swines, against FMDV.

12 Claims, 15 Drawing Sheets

Specification includes a Sequence Listing.

Figure 1

| SEQ ID NO: | Type | Gene Description |
|---|---|---|
| 1 | DNA | Polynucleotide encoding chimeric A24-A12 FMDV antigen |
| 2 | protein | Chimeric A24-A12 FMDV antigen |
| 3 | DNA | Polynucleotide encoding O1M FMDV antigen |
| 4 | protein | O1M FMDV antigen |
| 5 | DNA | Polynucleotide encoding Irn FMDV antigen |
| 6 | protein | Irn FMDV antigen |
| 7 | DNA | Polynucleotide encoding Asia FMDV antigen |
| 8 | protein | Asia FMDV antigen |

Figure 2
Foot and Mouth disease virus serotype A24, strain Cruzeiro

FMDV A24 strain Cruzeiro cDNA

5'UTR | L^pro | VP4 | VP2 | VP3 | VP1 | 2A | 2B | 2C | 3A | 3B | 3C^pro | 3D^pol | 3'UTR Poly(A)

VP4-VP2-VP3-VP1(P1)/2A/2B' cDNA fragment produced by PCR

SpeI → VP4 | VP2 | VP3 | HindIII → VP1 2A 2B'
HindIII →

A24 P1 = 2208 bp
A24 cDNA ≈ 2545 bp

A24 (P1-2AB') cDNA fragment used to construct the expression vector's structural capsid gene component Figure 3
Foot and mouth disease virus serotype A12, strain 119

FMDV A12 strain 119 cDNA
5' UTR | L^pro | VP4 | VP2 | VP3 | VP1 | 2A | 2B | 2C | 3A | 3B | 3C^pro | 3D^pol | 3' UTR Poly(A)

FMDV A12 3B'/3C protease cDNA fragment produced by PCR

3B' | 3C^pro

A12 3B'/3C ~836 bp
A12 3C ~642 bp

A12 (3B'C) cDNA fragment used to construct the expression vector's nonstructural capsid gene

Figure 4

Genetic structural identity assay of recombinant adenovirus vectored
A24-A12 FMDV vaccine by PCR Lane 1:     negative control
Lane 2:     positive control
Lane 3;     A24-A12 construct
Lane 4:     blank

Figure 5

Western blot of recombinant adenovirus vectored A24-A12 FMDV vaccine

40kD
30kD
20kD

Lane 1:   negative control
Lane 2:   positive control – shuttle plasmid
Lane 3:   recombinant adenovirus vectored chimeric A24-A12 FMDV vaccine Figure 6
Foot and mouth disease virus serotype O1/Man/87

5' UTR-IRES L^pro | VP4 | VP2 | VP3 | VP1 | 2A | 2B | 2C | 3A | 3B | 3C^pro | 3D^pol | 3' UTR Poly (A)

VP4 | VP2 | VP3 | VP1 | 2A | 2B | 2C'
← O1M P1/2ABC' = 2748 bp →

3A' | 3B | 3C^pro
← O1M 3A'BC = 837 bp →

VP4-VP2-VP3-VP1 (P1) / 2ABC' / 3A'BC sequence from FMD O1/Man/87

VP4 | VP2 | VP3 | VP1 | 2A | 2B | 2C' | 3A' | 3B | 3C^pro
← O1M87 transgene = 3585bp →

O1M87 transgene subcloned into shuttle plasmid for expression
of FMD structural and non-structural protein components Figure 7 Foot and mouth disease virus serotype A/Irn/05

| 5'UTR-IRES | L^pro | VP4 | VP2 | VP3 | VP1 | 2A | 2B | 2C | 3A | 3B | 3C^pro | 3D^pol | 3'UTR Poly(A) |

| VP4 | VP2 | VP3 | VP1 | 2A | 2B | 2C' |
AIrn05 P1/2ABC' = 2743 bp

| 3A' | 3B | 3C^pro |
AIrn05 3A'BC = 836 bp

VP4-VP2-VP3-VP1(P1) / 2ABC' / 3A'BC from FMD A/Irn/05 produced synthetically

| VP4 | VP2 | VP3 | VP1 | 2A | 2B | 2C' | 3A' | 3B | 3C^pro |
AIrn05 transgene = 3579 bp → AIrn05 transgene subcloned into shuttle plasmid for expression of FMD structural and non-structural protein components Figure 8 Foot and mouth disease virus serotype Asia/Leb/89

| 5'UTR-IRES | L^pro | VP4 | VP2 | VP3 | VP1 | 2A | 2B | 2C | 3A | 3B | 3C^pro | 3D^pol | 3'UTR Poly(A) |

| VP4 | VP2 | VP3 | VP1 | 2A | 2B | 2C' |

← Asia 1 P1/2ABC' = 2740 bp →

VP4-VP2-VP3-VP1(P1) / 2ABC' / 3A'BC sequence
from FMD Asia/Leb/89 produced synthetically

| 3A' | 3B | 3C^pro |

← Asia 1 3A'BC = 836 bp →

| VP4 | VP2 | VP3 | VP1 | 2A | 2B | 2C' | 3A' | 3B | 3C^pro |

← AsiaSS transgene = 3576 bp →

AsiaSS transgene subcloned into shuttle plasmid for expression
of FMD structural and non-structural protein components

Figure 9

Protection percentage O serotype FMDV vaccine at different doses

Figure 10

Serology of O serotype FMDV vaccine at different doses

Figure 13

Geometric Mean of FMDV VN log 10 Titer

Figure 15

Geometric Mean of FMDV VN log 10 Titer

SEQUENCE LISTING

```
<160> NUMBER OF SEQ ID NOS: 8

<210> SEQ ID NO 1
<211> LENGTH: 3381
<212> TYPE: DNA
<213> ORGANISM: artificial sequence
<220> FEATURE:
<223> OTHER INFORMATION: polynucleotide encoding chimeric A24-A12 FMDV
      antigen

<400> SEQUENCE: 1
atgaacacaa ctgactgttt tatcgctttg gtgcacgcaa tcagagagat cagagcactt       60
ttcctaccac gaaccacagg aaagatggaa ctcaccctgt acaacggcga gaaaaagact      120
ttctactcca gacctaacaa ccacgacaac tgttggttga acactgtcct tcagttgttc      180
aggtatgtcg atgagccctt cttcgactgg gtctacaact cacctgagaa cctcacgctc      240
gaagccatcg agcaattgga ggaactcaca ggacttgagc tgcacgaagg tgggccgccc      300
gccctcgtga tctggaacat caaacacttg ctccacaccg gcatcggcac agcctcacga      360
cccagtgagg tgtgcatggt ggacggtacg gacatgtgtc ttgccgactt ccacgcaggc      420
attttcctga agggacagga acacgcagtc tttgcatgtg tcacctccaa cgggtggtac      480
gcgattgatg atgaggaatt ttaccctgg acgcctgacc cgtcagacgt cctggtgttt      540
gtcccatacg accaagagcc actcaacggg gactggaaag cgatggtcca gaggaagctt      600
aagggcgccg ggcaatccag cccggcgacc ggctctcaga accagtctgg caacactggc      660
agcataatca taactacta catgcagcag taccagaact ccatggacac gcagcttggt      720
gacaatgcca tcagtggagg ctccaacgaa ggctccacgg acacaacgtc aacacacaca      780
accaacaccc aaaacaacga ctggtttcg aaacttgcca gctcagcctt taccggtctg      840
ttcggcgcct tgcttgccga caagaagacg gaagagacta cgcttctgga ggaccgcatt      900
ctcaccaccc gcaacgggca caccatctcg accacccagt cgagtgtggg agtcacctac      960
gggtactcca ctggagaaga ccacgttgct gggcccaaca catcgggcct ggagacgcgg     1020
gtggtgcagg ctgagagatt ttacaaaaag ttttttgtttg attggacaac ggataagcct     1080
tttggacatt tggaaaagtt ggaacttccc accgaccacc acggtgtttt cgggcacttg     1140
gtggaatcgt atgcctacat gagaaacggt tgggacgttg aggtgtctgc tgttggcaac     1200
cagttcaacg gcgggtgtct cctggtggct atggtaccgg agtggaagga gtttgaacaa     1260
cgtgagaagt accagctcac cctctttccc caccagttca ttagccccag aacaaacatg     1320
```

| | |
|---|---|
| actgcccaca ttactgtccc ataccttgga gtgaacaggt acgaccagta caagaaacac | 1380 |
| aaaccttgga ccctggttgt tatggtagtg tcgcccctta cagttagcag cactgccgcg | 1440 |
| gcacagatta aggtctacgc caacattgct ccaacctacg ttcacgtggc cggggaacta | 1500 |
| ccctcgaagg aggggatttt cccggttgca tgttcgacg gttacggagg actggtgaca | 1560 |
| acagacccga aaacagctga ccctgcctac ggcaaggtgt acaacccgcc caggaataac | 1620 |
| taccccgggc ggttcaccaa cttgttggac gtggctgaag cgtgtcccac tttcctctgt | 1680 |
| ttcgacgacg ggaaaccgta cgtcgttacg cggacagatg acacgcgact cttagccaag | 1740 |
| ttcgacgttt cccttgccgc aaaacacatg tccaacacgt acctgtcagg atagcacag | 1800 |
| tactatacac agtactctgg taccatcaac ttgcacttca tgtttacagg ttcaacagat | 1860 |
| tcaaaggccc gttacatggt ggcctacatc ccgcccgggg tggaagtgcc accgacaca | 1920 |
| cctgaaaggg ctgcccactg tatccacgct gaatgggaca caggactgaa ctccaaattc | 1980 |
| acttttttcaa tcccgtacgt gtccgccgca gattacgcgt acaccgcgtc tgacacggca | 2040 |
| gaaacaacca acgtacaggg ctgggtctgc atttaccaga ttacacacgg aaggccgag | 2100 |
| aacgacacac tagtcgtgtc ggccagcgcc ggcaaggact ttgagttgcg cctcccgatt | 2160 |
| gacccgcgac ggcaaaccac cgctgttggg gagtccgcag accctgtcac caccaccgtg | 2220 |
| gagaactacg gcggtgagac acagacccag aggcgacatc atacagatgt cagtttcatc | 2280 |
| atggacagat ttgtgaaaat aaaacagctt g agtcccacac atgtcattga cctcatgcag | 2340 |
| acccaccaac acgggctggt gggcgcgctg ctgcgtgcag ccacgtacta cttctccgac | 2400 |
| ttggagattg ttgtgcggca tgacggtaat ttgacttggg tgcccaacgg tgcgcctgaa | 2460 |
| gcagctttgt caaacaccag caaccccact gcctacaaca aggcaccgtt cacgaggctc | 2520 |
| gctctcccctt acactgcgcc acaccgggcg tgtaatgacg tgaactccga gcctgcccgg | 2580 |
| cccgctgaag agcaaccaca agctgaagga ccctataccg gccactcga gcgtcagaga | 2640 |
| cctctgaaag tgagagctaa gctcccacag caggaaggac cttacgctgg cccgttggag | 2700 |
| agacagaaac cgctgaaagt gaaagcaaaa gccccggtcg tcaaggaagg accttacgag | 2760 |
| ggaccggtga agaagcctgt cgctttgaaa gtgaaagcta agaacttgat agtcactgag | 2820 |
| agtggtgccc caccgaccga cttgcaaaag atggtcatgg gcaacacaaa gcctgttgag | 2880 |
| ctcatccttg acgggaagac agtagccatc tgttgtgcta ctggagtgtt tggcactgct | 2940 |
| tacctcgtgc ctcgtcatct tttcgcagag aagtatgaca agatcatgct ggatggcaga | 3000 |
| gccatgacag acagtgacta cagagtgttt gagtttgaga ttaaagtaaa aggacaggac | 3060 |
| atgctctcag acgctgcgct catggtgctc caccgtggga accgcgtgag agatatcacg | 3120 |
| aaacactttc gtgatacagc aagaatgaag aaaggcaccc ccgtcgtcgg tgtggtcaac | 3180 |
| aacgccgacg ttgggagact gattttctct ggtgaggccc tcacctacaa ggatattgta | 3240 |
| gtgtgcatgg acggagacac catgcctggc ctctttgcct acaaagccgc caccaaggca | 3300 |
| ggctactgtg gaggagccgt tctcgccaag gacgggccg acactttcat cgtcggcact | 3360 |
| cactccgcag gaggcaatgg a | 3381 |

<210> SEQ ID NO 2
<211> LENGTH: 1127
<212> TYPE: PRT
<213> ORGANISM: artificial sequence
<220> FEATURE:
<223> OTHER INFORMATION: chimeric A24-A12 FMDV antigen A24 P1-2A2B/A12 3B3C

<400> SEQUENCE: 2

Met Asn Thr Thr Asp Cys Phe Ile Ala Leu Val His Ala Ile Arg Glu
1               5                   10                  15

Ile Arg Ala Leu Phe Leu Pro Arg Thr Thr Gly Lys Met Glu Leu Thr
            20                  25                  30

Leu Tyr Asn Gly Glu Lys Lys Thr Phe Tyr Ser Arg Pro Asn Asn His
        35                  40                  45

Asp Asn Cys Trp Leu Asn Thr Val Leu Gln Leu Phe Arg Tyr Val Asp
    50                  55                  60

Glu Pro Phe Phe Asp Trp Val Tyr Asn Ser Pro Glu Asn Leu Thr Leu
65                  70                  75                  80

Glu Ala Ile Glu Gln Leu Glu Glu Leu Thr Gly Leu Glu Leu His Glu
                85                  90                  95

Gly Gly Pro Pro Ala Leu Val Ile Trp Asn Ile Lys His Leu Leu His
            100                 105                 110

Thr Gly Ile Gly Thr Ala Ser Arg Pro Ser Glu Val Cys Met Val Asp
        115                 120                 125

Gly Thr Asp Met Cys Leu Ala Asp Phe His Ala Gly Ile Phe Leu Lys
    130                 135                 140

Gly Gln Glu His Ala Val Phe Ala Cys Val Thr Ser Asn Gly Trp Tyr
145                 150                 155                 160

Ala Ile Asp Asp Glu Glu Phe Tyr Pro Trp Thr Pro Asp Pro Ser Asp
                165                 170                 175

Val Leu Val Phe Val Pro Tyr Asp Gln Glu Pro Leu Asn Gly Asp Trp
            180                 185                 190

Lys Ala Met Val Gln Arg Lys Leu Lys Gly Ala Gly Gln Ser Ser Pro
        195                 200                 205

Ala Thr Gly Ser Gln Asn Gln Ser Gly Asn Thr Gly Ser Ile Ile Asn
    210                 215                 220

Asn Tyr Tyr Met Gln Gln Tyr Gln Asn Ser Met Asp Thr Gln Leu Gly
225                 230                 235                 240

Asp Asn Ala Ile Ser Gly Gly Ser Asn Glu Gly Ser Thr Asp Thr Thr
                245                 250                 255

Ser Thr His Thr Thr Asn Thr Gln Asn Asn Asp Trp Phe Ser Lys Leu
            260                 265                 270

Ala Ser Ser Ala Phe Thr Gly Leu Phe Gly Ala Leu Leu Ala Asp Lys
        275                 280                 285

Lys Thr Glu Glu Thr Thr Leu Leu Glu Asp Arg Ile Leu Thr Thr Arg
    290                 295                 300

Asn Gly His Thr Ile Ser Thr Thr Gln Ser Ser Val Gly Val Thr Tyr
305                 310                 315                 320

Gly Tyr Ser Thr Gly Glu Asp His Val Ala Gly Pro Asn Thr Ser Gly
                325                 330                 335

Leu Glu Thr Arg Val Val Gln Ala Glu Arg Phe Tyr Lys Lys Phe Leu
            340                 345                 350

Phe Asp Trp Thr Thr Asp Lys Pro Phe Gly His Leu Glu Lys Leu Glu
        355                 360                 365

Leu Pro Thr Asp His His Gly Val Phe Gly His Leu Val Glu Ser Tyr
    370                 375                 380

Ala Tyr Met Arg Asn Gly Trp Asp Val Glu Val Ser Ala Val Gly Asn
385                 390                 395                 400

Gln Phe Asn Gly Gly Cys Leu Leu Val Ala Met Val Pro Glu Trp Lys

```
                405                 410                 415
Glu Phe Glu Gln Arg Glu Lys Tyr Gln Leu Thr Leu Phe Pro His Gln
            420                 425                 430

Phe Ile Ser Pro Arg Thr Asn Met Thr Ala His Ile Thr Val Pro Tyr
            435                 440                 445

Leu Gly Val Asn Arg Tyr Asp Gln Tyr Lys His Lys Pro Trp Thr
            450                 455                 460

Leu Val Val Met Val Val Ser Pro Leu Thr Val Ser Thr Ala Ala
465                 470                 475                 480

Ala Gln Ile Lys Val Tyr Ala Asn Ile Ala Pro Thr Tyr Val His Val
                485                 490                 495

Ala Gly Glu Leu Pro Ser Lys Glu Gly Ile Phe Pro Val Ala Cys Ser
            500                 505                 510

Asp Gly Tyr Gly Gly Leu Val Thr Thr Asp Pro Lys Thr Ala Asp Pro
            515                 520                 525

Ala Tyr Gly Lys Val Tyr Asn Pro Pro Arg Asn Asn Tyr Pro Gly Arg
            530                 535                 540

Phe Thr Asn Leu Leu Asp Val Ala Glu Ala Cys Pro Thr Phe Leu Cys
545                 550                 555                 560

Phe Asp Asp Gly Lys Pro Tyr Val Val Thr Arg Thr Asp Thr Arg
                565                 570                 575

Leu Leu Ala Lys Phe Asp Val Ser Leu Ala Ala Lys His Met Ser Asn
            580                 585                 590

Thr Tyr Leu Ser Gly Ile Ala Gln Tyr Tyr Thr Gln Tyr Ser Gly Thr
            595                 600                 605

Ile Asn Leu His Phe Met Phe Thr Gly Ser Thr Asp Ser Lys Ala Arg
            610                 615                 620

Tyr Met Val Ala Tyr Ile Pro Pro Gly Val Glu Val Pro Pro Asp Thr
625                 630                 635                 640

Pro Glu Arg Ala Ala His Cys Ile His Ala Glu Trp Asp Thr Gly Leu
                645                 650                 655

Asn Ser Lys Phe Thr Phe Ser Ile Pro Tyr Val Ser Ala Ala Asp Tyr
            660                 665                 670

Ala Tyr Thr Ala Ser Asp Thr Ala Glu Thr Thr Asn Val Gln Gly Trp
            675                 680                 685

Val Cys Ile Tyr Gln Ile Thr His Gly Lys Ala Glu Asn Asp Thr Leu
            690                 695                 700

Val Val Ser Ala Ser Ala Gly Lys Asp Phe Glu Leu Arg Leu Pro Ile
705                 710                 715                 720

Asp Pro Arg Arg Gln Thr Thr Ala Val Gly Glu Ser Ala Asp Pro Val
                725                 730                 735

Thr Thr Thr Val Glu Asn Tyr Gly Gly Glu Thr Gln Thr Gln Arg Arg
            740                 745                 750

His His Thr Asp Val Ser Phe Ile Met Asp Arg Phe Val Lys Ile Asn
            755                 760                 765

Ser Leu Ser Pro Thr His Val Ile Asp Leu Met Gln Thr His Gln His
770                 775                 780

Gly Leu Val Gly Ala Leu Leu Arg Ala Ala Thr Tyr Tyr Phe Ser Asp
785                 790                 795                 800

Leu Glu Ile Val Val Arg His Asp Gly Asn Leu Thr Trp Val Pro Asn
                805                 810                 815

Gly Ala Pro Glu Ala Ala Leu Ser Asn Thr Ser Asn Pro Thr Ala Tyr
            820                 825                 830
```

Asn Lys Ala Pro Phe Thr Arg Leu Ala Leu Pro Tyr Thr Ala Pro His
   835                 840                 845

Arg Ala Cys Asn Asp Val Asn Ser Glu Pro Ala Arg Pro Ala Glu Glu
850                 855                 860

Gln Pro Gln Ala Glu Gly Pro Tyr Thr Gly Pro Leu Glu Arg Gln Arg
865                 870                 875                 880

Pro Leu Lys Val Arg Ala Lys Leu Pro Gln Gln Glu Gly Pro Tyr Ala
                885                 890                 895

Gly Pro Leu Glu Arg Gln Lys Pro Leu Lys Val Lys Ala Lys Ala Pro
            900                 905                 910

Val Val Lys Glu Gly Pro Tyr Glu Gly Pro Val Lys Lys Pro Val Ala
        915                 920                 925

Leu Lys Val Lys Ala Lys Asn Leu Ile Val Thr Glu Ser Gly Ala Pro
    930                 935                 940

Pro Thr Asp Leu Gln Lys Met Val Met Gly Asn Thr Lys Pro Val Glu
945                 950                 955                 960

Leu Ile Leu Asp Gly Lys Thr Val Ala Ile Cys Cys Ala Thr Gly Val
                965                 970                 975

Phe Gly Thr Ala Tyr Leu Val Pro Arg His Leu Phe Ala Glu Lys Tyr
            980                 985                 990

Asp Lys Ile Met Leu Asp Gly Arg Ala Met Thr Asp Ser Asp Tyr Arg
        995                 1000                1005

Val Phe Glu Phe Glu Ile Lys Val Lys Gly Gln Asp Met Leu Ser
    1010                1015                1020

Asp Ala Ala Leu Met Val Leu His Arg Gly Asn Arg Val Arg Asp
    1025                1030                1035

Ile Thr Lys His Phe Arg Asp Thr Ala Arg Met Lys Lys Gly Thr
    1040                1045                1050

Pro Val Val Gly Val Val Asn Asn Ala Asp Val Gly Arg Leu Ile
    1055                1060                1065

Phe Ser Gly Glu Ala Leu Thr Tyr Lys Asp Ile Val Val Cys Met
    1070                1075                1080

Asp Gly Asp Thr Met Pro Gly Leu Phe Ala Tyr Lys Ala Ala Thr
    1085                1090                1095

Lys Ala Gly Tyr Cys Gly Gly Ala Val Leu Ala Lys Asp Gly Ala
    1100                1105                1110

Asp Thr Phe Ile Val Gly Thr His Ser Ala Gly Gly Asn Gly
    1115                1120                1125

<210> SEQ ID NO 3
<211> LENGTH: 3585
<212> TYPE: DNA
<213> ORGANISM: artificial sequence
<220> FEATURE:
<223> OTHER INFORMATION: synthetic polynucleotide encoding FMDV O1M87
      antigen

<400> SEQUENCE: 3
atgggagccg gcaatccag cccggcaacc gggtcacaga accaatcagg caacactggg      60
agcatcatca caattacta catgcagcag taccaaaact ccatggacac acaacttggt     120
gacaacgcta caagcggagg ctcaaacgag gggtccacgg acacaacctc caccacaca    180 accaacactc agaacaacga ctggttctcg aagctggcca gttccgcttt cagcggtctt     240
ttcggcgctc ttctcgccga caagaaaacc gaggagacca ctcttctcga ggaccgcatc     300
ctcactactc gtaacggaca caccacctcg acaacccagt cgagcgttgg agtcacgtac      360
gggtatgcaa cagctgagga tttcgtgagc gggccaaaca cctctggtct cgagaccagg      420
gttgcccagg cagagcggtt ctttaaaacc cacctgttcg actgggtcac cagtgacccg      480
ttcggacggt gccacctgct ggaacttcca actgaccaca aaggtgtcta cggcagcctg      540
accgactcgt atgcttatat gaggaacggc tgggatgttg aagtcactgc agtgggaaac      600
cagttcaatg gaggatgcct gttggtggcc atggtgccag aactttgctc catacagaag      660
agggagctgt accagctcac gctctttcct caccagttca tcaaccctcg gacgaacatg      720
acagcacaca tcactgtgcc ctttgttggc gtcaaccgtt atgaccagta caaggtacac      780
aaaccttgga ccctcgtggt tatggttgta gcccccctga ccgtcaacag tgaaggtgcc      840
ccgcaaatca aggtgtatgc caacatcgca cctaccaacg tacacgtcgc gggtgagttc      900
ccttccaaag agggatctt ccctgtggct tgcagcgatg gttatggcgg tctggtgacc       960
actgacccga aaacggctga ccccgcttac gggaaagtgt taaccccccc cgcaacatg      1020 ttgccggggc ggttcaccaa tttcttgac gtggctgagg cgtgccccac gtttctccac      1080
ttcgagggtg acgtgccata cgtgaccacg aagacggatt cagacagggt gctcgctcag      1140
ttcgacttgt ctttggcagc aaagcacatg tcgaacacct ccttgcagg tctcgcccag      1200 tactacacac agtacagcgg caccatcaac ctgcacttca tgttcacagg gcctactgac      1260
gcgaaggcgc gttacatgat tgcgtatgct cctcctggca tggaaccacc taaaacgcca      1320
gaggcggctg cccactgcat tcatgctgaa tgggacacag ggttgaactc aaaattcaca      1380
ttttcaatcc cttaccttc ggcggctgat tacgcttaca cagcgtctga cactgctgag      1440
accacaaatg tacagggatg ggtttgcctg tttcaaataa cacacgggaa agctgacggc      1500
gacgcactgg tcgttttggc tagcgccgga aaggactttg agctgcgcct gccggtggat      1560
gctcgcacac agactacctc cgcgggcgag tcagctgacc ccgtgaccgc caccgttgag      1620
aattacggtg gcgagacaca ggtccagagg cgccaacaca cggacgtctc atttatatta      1680
gacagatttg tgaaagtgac accaaaagac caaattaatg tattggaccc tgatgcaaacc      1740 cctgctcaca ctttggtggg agcactcctt cgtactgcca cttactattt cgctgactta      1800
gaggtggcag tgaagcacga gggaaacctc acctgggtcc cgaacggggc gcctgaagcg      1860
gcgttggaca caccaccaa cccaacagct taccacaagg caccactcac ccgacttgca       1920
ctgccttaca cggcgccaca ccgcgtgttg gctactgttt acaacgggaa cagcaagtat      1980
ggtgacggca cggtggccaa tgtgagaggt gacctgcaag tgttggccca gaaggcggcg      2040
agagcgctgc ctacctcctt caactacggt gccattaaag ctactcgggt gactgaactg      2100
ctttaccgca tgaagagggc tgagacatac tgtccccggc ctcttttggc cattcacccg      2160
gaccaggcta gacacaagca gaagattgtg cacccggtga acagcttct aaatttttgac      2220 ctgctcaaat tggcgggaga tgtggagtcc aaccctgggc cttcttctt ctccgacgtc       2280 aggtcaaatt tctcaaaact ggtagaaacc atcaatcaga tgcaggagga catgtcaaca      2340
aaacacgggc tgactttaa ccggttggtg tccgcatttg aggaattggc cactggagtg       2400
aaggctatca gggccggtct cgacgaggcc aaaccctggt acaaactcat caagctcctg      2460
agccgcttgt catgcatggc cgctgtagca gcacggtcaa aggacccagt ccttgtggcc      2520
atcatgctgg ctgacaccgg tcttgagatt ctggacagca cctttgtcgt gaagaagatc      2580
tccgactcgc tctccagtct cttcacgtg ccggcccccg tcttcagttt cggagccccg       2640
attctgttgg ccgggttggt caaagtcgcc tcgagtttct tccggtccac acccgaagac      2700

-continued

```
cttgagagag cagaaaaaca gctcaaagca cgtgacatta acgacatact tgagcgtcag    2760
aaacctctga gagtgaaaac caagttgcca caacaggagg accctacgc tggcccgatg    2820 gatagacaga aaccgttgaa agtgagagca agagccccgg tcgtgaagga gggaccctac    2880
gagggaccgg tgaagaagcc tgtcgctttg aaagtgaaag ccaagaactt gattgtcact    2940
gagagtggtg ccccaccgac cgacttgcag aagatggtca tgggcaacac taagcctgtt    3000
gagctcatcc tcgacgggaa gacggtagcc atctgctgtg ctaccggagt gtttggcact    3060
gcctacctcg tacctcgtca cctcttcgcg gagaagtacg acaagataat gttggacggt    3120
agagccatga cagacagtga ctacagagtg tttgagtttg agattaaagt aaaaggacag    3180
gacatgctct cagacgctgc actcatggtg cttcaccgtg ggaaccgcgt gagagacatc    3240
acgaaacatt ttcgtgacac agcaagaatg aagaaaggca ccccgttgt cggtgtgatc    3300 aacaacgccg acgttgggag actgattttc tctggagagg cccttaccta caaagacatt    3360
gtagtgtgca tggatggaga caccatgccg ggcctgtttg cctacagagc cgccaccaag    3420
gctggttact gcgggggagc cgttctcgcc aaggacggag ccgacacatt catcgttggc    3480
actcactccg caggtggtaa cggagttgga tactgctcgt gcgtgtccag gtccatgctc    3540
ctgaaaatga aggcacacat tgaccctgaa ccacaccacg agtag                    3585
```

<210> SEQ ID NO 4
<211> LENGTH: 1194
<212> TYPE: PRT
<213> ORGANISM: artificial sequence
<220> FEATURE:
<223> OTHER INFORMATION: FMDV O1M87 antigen

<400> SEQUENCE: 4

```
Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
            20                  25                  30

Asn Ser Met Asp Thr Gln Leu Gly Asp Asn Ala Thr Ser Gly Gly Ser
        35                  40                  45

Asn Glu Gly Ser Thr Asp Thr Thr Ser Thr His Thr Thr Asn Thr Gln
    50                  55                  60

Asn Asn Asp Trp Phe Ser Lys Leu Ala Ser Ser Ala Phe Ser Gly Leu
65                  70                  75                  80

Phe Gly Ala Leu Leu Ala Asp Lys Lys Thr Glu Glu Thr Thr Leu Leu
                85                  90                  95

Glu Asp Arg Ile Leu Thr Thr Arg Asn Gly His Thr Thr Ser Thr Thr
            100                 105                 110

Gln Ser Ser Val Gly Val Thr Tyr Gly Tyr Ala Thr Ala Glu Asp Phe
        115                 120                 125

Val Ser Gly Pro Asn Thr Ser Gly Leu Glu Thr Arg Val Ala Gln Ala
    130                 135                 140

Glu Arg Phe Phe Lys Thr His Leu Phe Asp Trp Val Thr Ser Asp Pro
145                 150                 155                 160

Phe Gly Arg Cys His Leu Leu Glu Leu Pro Thr Asp His Lys Gly Val
                165                 170                 175

Tyr Gly Ser Leu Thr Asp Ser Tyr Ala Tyr Met Arg Asn Gly Trp Asp
            180                 185                 190

Val Glu Val Thr Ala Val Gly Asn Gln Phe Asn Gly Gly Cys Leu Leu
        195                 200                 205
```

-continued

```
Val Ala Met Val Pro Glu Leu Cys Ser Ile Gln Lys Arg Glu Leu Tyr
    210                 215                 220
Gln Leu Thr Leu Phe Pro His Gln Phe Ile Asn Pro Arg Thr Asn Met
225                 230                 235                 240
Thr Ala His Ile Thr Val Pro Phe Val Gly Val Asn Arg Tyr Asp Gln
                245                 250                 255
Tyr Lys Val His Lys Pro Trp Thr Leu Val Val Met Val Val Ala Pro
                260                 265                 270
Leu Thr Val Asn Ser Glu Gly Ala Pro Gln Ile Lys Val Tyr Ala Asn
                275                 280                 285
Ile Ala Pro Thr Asn Val His Val Ala Gly Phe Pro Ser Lys Glu
    290                 295                 300
Gly Ile Phe Pro Val Ala Cys Ser Asp Gly Tyr Gly Gly Leu Val Thr
305                 310                 315                 320
Thr Asp Pro Lys Thr Ala Asp Pro Ala Tyr Gly Lys Val Phe Asn Pro
                325                 330                 335
Pro Arg Asn Met Leu Pro Gly Arg Phe Thr Asn Phe Leu Asp Val Ala
                340                 345                 350
Glu Ala Cys Pro Thr Phe Leu His Phe Glu Gly Asp Val Pro Tyr Val
            355                 360                 365
Thr Thr Lys Thr Asp Ser Asp Arg Val Leu Ala Gln Phe Asp Leu Ser
    370                 375                 380
Leu Ala Ala Lys His Met Ser Asn Thr Phe Leu Ala Gly Leu Ala Gln
385                 390                 395                 400
Tyr Tyr Thr Gln Tyr Ser Gly Thr Ile Asn Leu His Phe Met Phe Thr
                405                 410                 415
Gly Pro Thr Asp Ala Lys Ala Arg Tyr Met Ile Ala Tyr Ala Pro Pro
                420                 425                 430
Gly Met Glu Pro Pro Lys Thr Pro Glu Ala Ala Ala His Cys Ile His
            435                 440                 445
Ala Glu Trp Asp Thr Gly Leu Asn Ser Lys Phe Thr Phe Ser Ile Pro
    450                 455                 460
Tyr Leu Ser Ala Ala Asp Tyr Ala Tyr Thr Ala Ser Asp Thr Ala Glu
465                 470                 475                 480
Thr Thr Asn Val Gln Gly Trp Val Cys Leu Phe Gln Ile Thr His Gly
                485                 490                 495
Lys Ala Asp Gly Asp Ala Leu Val Val Leu Ala Ser Ala Gly Lys Asp
                500                 505                 510
Phe Glu Leu Arg Leu Pro Val Asp Ala Arg Thr Gln Thr Thr Ser Ala
            515                 520                 525
Gly Glu Ser Ala Asp Pro Val Thr Ala Thr Val Glu Asn Tyr Gly Gly
    530                 535                 540
Glu Thr Gln Val Gln Arg Arg His Thr Asp Val Ser Phe Ile Leu
545                 550                 555                 560
Asp Arg Phe Val Lys Val Thr Pro Lys Asp Gln Ile Asn Val Leu Asp
                565                 570                 575
Leu Met Gln Thr Pro Ala His Thr Leu Val Gly Ala Leu Leu Arg Thr
            580                 585                 590
Ala Thr Tyr Tyr Phe Ala Asp Leu Glu Val Ala Val Lys His Glu Gly
    595                 600                 605
Asn Leu Thr Trp Val Pro Asn Gly Ala Pro Glu Ala Ala Leu Asp Asn
    610                 615                 620
```

```
Thr Thr Asn Pro Thr Ala Tyr His Lys Ala Pro Leu Thr Arg Leu Ala
625                 630                 635                 640

Leu Pro Tyr Thr Ala Pro His Arg Val Leu Ala Thr Val Tyr Asn Gly
                645                 650                 655

Asn Ser Lys Tyr Gly Asp Gly Thr Val Ala Asn Val Arg Gly Asp Leu
            660                 665                 670

Gln Val Leu Ala Gln Lys Ala Ala Arg Ala Leu Pro Thr Ser Phe Asn
        675                 680                 685

Tyr Gly Ala Ile Lys Ala Thr Arg Val Thr Glu Leu Leu Tyr Arg Met
    690                 695                 700

Lys Arg Ala Glu Thr Tyr Cys Pro Arg Pro Leu Leu Ala Ile His Pro
705                 710                 715                 720

Asp Gln Ala Arg His Lys Gln Lys Ile Val Ala Pro Val Lys Gln Leu
                725                 730                 735

Leu Asn Phe Asp Leu Leu Lys Leu Ala Gly Asp Val Glu Ser Asn Pro
            740                 745                 750

Gly Pro Phe Phe Phe Ser Asp Val Arg Ser Asn Phe Ser Lys Leu Val
        755                 760                 765

Glu Thr Ile Asn Gln Met Gln Glu Asp Met Ser Thr Lys His Gly Pro
    770                 775                 780

Asp Phe Asn Arg Leu Val Ser Ala Phe Glu Glu Leu Ala Thr Gly Val
785                 790                 795                 800

Lys Ala Ile Arg Ala Gly Leu Asp Glu Ala Lys Pro Trp Tyr Lys Leu
                805                 810                 815

Ile Lys Leu Leu Ser Arg Leu Ser Cys Met Ala Ala Val Ala Ala Arg
            820                 825                 830

Ser Lys Asp Pro Val Leu Val Ala Ile Met Leu Ala Asp Thr Gly Leu
        835                 840                 845

Glu Ile Leu Asp Ser Thr Phe Val Val Lys Lys Ile Ser Asp Ser Leu
    850                 855                 860

Ser Ser Leu Phe His Val Pro Ala Pro Val Phe Ser Phe Gly Ala Pro
865                 870                 875                 880

Ile Leu Leu Ala Gly Leu Val Lys Val Ala Ser Ser Phe Phe Arg Ser
                885                 890                 895

Thr Pro Glu Asp Leu Glu Arg Ala Glu Lys Gln Leu Lys Ala Arg Asp
            900                 905                 910

Ile Asn Asp Ile Leu Glu Arg Gln Lys Pro Leu Arg Val Lys Thr Lys
        915                 920                 925

Leu Pro Gln Gln Glu Gly Pro Tyr Ala Gly Pro Met Asp Arg Gln Lys
    930                 935                 940

Pro Leu Lys Val Arg Ala Arg Ala Pro Val Val Lys Glu Gly Pro Tyr
945                 950                 955                 960

Glu Gly Pro Val Lys Lys Pro Val Ala Leu Lys Val Lys Ala Lys Asn
                965                 970                 975

Leu Ile Val Thr Glu Ser Gly Ala Pro Pro Thr Asp Leu Gln Lys Met
            980                 985                 990

Val Met Gly Asn Thr Lys Pro Val Glu Leu Ile Leu Asp Gly Lys Thr
        995                 1000                1005

Val Ala Ile Cys Cys Ala Thr Gly Val Phe Gly Thr Ala Tyr Leu
        1010                1015                1020

Val Pro Arg His Leu Phe Ala Glu Lys Tyr Asp Lys Ile Met Leu
    1025                1030                1035

Asp Gly Arg Ala Met Thr Asp Ser Asp Tyr Arg Val Phe Glu Phe
```

| | | | | | | | | | | |
|---|---|---|---|---|---|---|---|---|---|---|
| | | 1040 | | | 1045 | | | 1050 | | |
| Glu | Ile | Lys | Val | Lys | Gly | Gln | Asp | Met | Leu | Ser | Asp | Ala | Ala | Leu |
| | 1055 | | | | 1060 | | | | 1065 | |
| Met | Val | Leu | His | Arg | Gly | Asn | Arg | Val | Arg | Asp | Ile | Thr | Lys | His |
| | 1070 | | | | 1075 | | | | 1080 | |
| Phe | Arg | Asp | Thr | Ala | Arg | Met | Lys | Lys | Gly | Thr | Pro | Val | Val | Gly |
| | 1085 | | | | 1090 | | | | 1095 | |
| Val | Ile | Asn | Asn | Ala | Asp | Val | Gly | Arg | Leu | Ile | Phe | Ser | Gly | Glu |
| | 1100 | | | | 1105 | | | | 1110 | |
| Ala | Leu | Thr | Tyr | Lys | Asp | Ile | Val | Val | Cys | Met | Asp | Gly | Asp | Thr |
| | 1115 | | | | 1120 | | | | 1125 | |
| Met | Pro | Gly | Leu | Phe | Ala | Tyr | Arg | Ala | Ala | Thr | Lys | Ala | Gly | Tyr |
| | 1130 | | | | 1135 | | | | 1140 | |
| Cys | Gly | Gly | Ala | Val | Leu | Ala | Lys | Asp | Gly | Ala | Asp | Thr | Phe | Ile |
| | 1145 | | | | 1150 | | | | 1155 | |
| Val | Gly | Thr | His | Ser | Ala | Gly | Gly | Asn | Gly | Val | Gly | Tyr | Cys | Ser |
| | 1160 | | | | 1165 | | | | 1170 | |
| Cys | Val | Ser | Arg | Ser | Met | Leu | Leu | Lys | Met | Lys | Ala | His | Ile | Asp |
| | 1175 | | | | 1180 | | | | 1185 | |
| Pro | Glu | Pro | His | His | Glu |
| | 1190 | | | | |

```
<210> SEQ ID NO 5
<211> LENGTH: 3579
<212> TYPE: DNA
<213> ORGANISM: artificial sequence
<220> FEATURE:
<223> OTHER INFORMATION: Polynucleotide encoding Irn FMDV antigen

<400> SEQUENCE: 5
atgggagccg gcaatccag  tccggcaacc gggtcacaaa accaatcagg taacactggt     60
agtatcatca caactacta  catgcagcag taccagaact ccatggacac acaacttggc    120
gacaacgcca ttagcggtgg ttccaacgag gctccactg acactacctc cacacacaca    180
accaacacac agaacaatga ttggttttca aaattggcca gttctgcctt cagcggtctc    240
ttcggcgctc ttctcgctga caaaaagaca gaggagacta ccctcctgga agaccgcatc    300
ctcaccaccc gcaacggaca caccacctcg acaacacagt cgagtgtggg agtcacctac    360
gggtactcca ctggggaaga ccacgtctct ggacctaaca catctggcct ggagacgcga    420
gtggtacagg cagagagatt cttcaagaaa cacttgtttg attggacaac cgataaagct    480
tttggacacc tggaaaaact ggaactcccc actgaacaca agggtgtcta cgggcacttg    540
gtggactctt tcgcatacat gagaaatggc tgggacgtgg aggtgaccgc cgttggcaac    600
cagttcaacg gtgggtgtct cctggtggcc atggtacctg agtggaaaga gtttacccct    660
cgtgagaaat accagctcac cctgtttcca ccaattta tcaacccag aaccaacatg     720
acagcccaca tcacggtccc gtaccttggt gtcaataggg atgaccagta caaacagcac    780
aaaccctgga cactggtcgt gatggtggtt cgccactga ccaccagcag cattggagct    840
tcacagatca aggtctacgc caacattgcc ccaaccttcg ttcacgtggc cggcgagctc    900
ccatcgaagg aagggatcgt gccggttgct tgttcagacg ggtacggtgg cctggtgaca    960
acagacccga aaacagctga ccctgtttat ggtatggtct acaacccgcc cagaaccaac   1020
taccctgggc gctttacaaa cttgttggac gtggccgagg cttgcccgac cttcctctgt   1080
tttgacgacg ggaaaccgta cgttgtgaca aggacggacg accaacgtct cctggccaag   1140
```

```
tttgacgttt ctcttgctgc aaagcacatg tcaaacacct acctctcagg gatagcacag    1200
tactacacac agtactctgg cactatcaat ctgcacttca tgttcactgg ctctactgaa    1260
tcaaaggccc ggtacatggt ggcgtacatt ccacctggca tggacacgcc accggacaca    1320
cctgagaagg ctgcacattg catccacgcc gagtgggaca ccgggctgaa ctccaaattt    1380 acttttcta tcccgtacgt gtctgctgca gactacgcat acactgcgtc tgacgtggca    1440
gaaacaacaa acgtacaggg gtgggtctgc atataccaaa tcacccacgg gaaggctgag    1500
caggacactc tggtcgtgtc ggtcagcgcc ggcaaggact ttgaactgcg cctcccaatt    1560
gacccccgca cgcaaaccac cactgccggg gagtcagcag accctgtcac caccaccgtt    1620
gagaactacg gtggtgagac acaggctcag cgacgccagc acactgacgt cggcttcatc    1680
atggacaggt ttgtgaaaat cagccccgtg agccccacgc acgtcattga cctcatgcaa    1740
acacaccaac acgcgttggt gggtgcccctt ttgcgtgcag ccacgtacta cttctccgat    1800
ctggagatcg tggtgcgtca tgatggtaac ttgacgtggg tgcccaatgg agcacctgta    1860
gaagccttgg ccaacacaag caaccccacc gcctaccaca agcagccatt tacgagactt    1920
gcgctccctt acaccgcgcc gcaccgagtg ttggcaacag tgtataacgg agtaagcaag    1980
tactctacaa ctggtaatgg tagaagggggt gacctggggc ctcttgcggc gcgggtcgcc    2040
gcacagctcc ccagctcttt caactttggt gcaattcggg ccacgaccat ccacgagctt    2100
ctcgtgcgca tgaaacgtgc cgagctctac tgtcccaggc ctctgctggc agtggaagtg    2160
ttgtcgcagg acagacacaa gcaaaagatc attgcaccta caaagcaact cctgaacttc    2220
gacctgctca agttggcggg agacgtcgag tccaaccctg ggcccttctt cttctctgac    2280
gtcaggacga acttttctaa gctggttgac accatcaacc agatgcagga ggacatgtca    2340
acaaaacacg ggcccgactt taaccggttg gtgtctgcgt ttgaggaatt ggccgctgga    2400
gtgaaagcta tcaggaccgg tctcgacgag gccaagccct ggtacaagct cattaagctc    2460
ctgagccgcc tgtcatgcat ggccgctgta gcagcacggt caaaggaccc agtccttgtg    2520
gccatcatgc tagctgacac cggtctcgag attctggaca gcacctttgt cgtgaagaag    2580
atctccgact cgctctccag tctctttcac gtgccggccc ccgtcttcag cttcggagcc    2640
ccgattctgc tggccgggtt ggtcaaagtc gcctcgagtt tcttccggtc cacacccgaa    2700
gaccttgaga gagcagagaa acagctcaaa gcacgtgaca tcatcgagcg tcagaaacct    2760
ctgaaagtga gagccaagct cccacagcag gaggggccct acgctggtcc gatggagaga    2820
caaaagcccc tgaaagtgaa agcaaaagcc ccggtcgtaa aggaaggacc ttacgagggg    2880
cttgtgaaga aacctgtcgc tttgaaagtg aaagccaaaa atttgattgt cactgagagt    2940
ggtgcccccc cgaccgactt gcaaaagatg gtcatgggca acaccaagcc tgttgagctc    3000
atcctcgacg ggaagacggt agccatctgt tgcgctaccg gagtgtttgg cactgcttac    3060
cttgtaccac gtcatctttt cgcggagaag tatgacaaga tcatgctgga cggcagagcc    3120
atgacagaca gtgactacag agtgtttgag tttgagatta agtaaaaagg acaggacatg    3180
ctttcagatg ccgcgctcat ggtgctccac cgtgggaatc gcgtgagaga tatcacgaaa    3240
cactttcgtg acacagcaag aatgaagaag gcaccccccg ttgtcggtgt tatcaacaac    3300
gccgatgtcg ggagactgat tttctctggt gaggcccctta cctacaagga cattgtagtg    3360
tgtatggatg agacaccat gcctggcctc tttgcctaca gagccgccac caaggctggc    3420
tattgtggag gagctgttct tgcaaaggac ggagccgaga cttcatcgt cggcactcac    3480
```

-continued

```
tccgcaggcg gtaatggagt tggatactgt tcatgcgttt ccaggtccat gctgctaaag    3540
atgaaggcac acattgaccc tgagccacac cacgagtaa                           3579
```

<210> SEQ ID NO 6
<211> LENGTH: 1192
<212> TYPE: PRT
<213> ORGANISM: artificial sequence
<220> FEATURE:
<223> OTHER INFORMATION: Irn FMDV antigen

<400> SEQUENCE: 6

```
Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
            20                  25                  30

Asn Ser Met Asp Thr Gln Leu Gly Asp Asn Ala Ile Ser Gly Gly Ser
        35                  40                  45

Asn Glu Gly Ser Thr Asp Thr Thr Ser Thr His Thr Thr Asn Thr Gln
    50                  55                  60

Asn Asn Asp Trp Phe Ser Lys Leu Ala Ser Ser Ala Phe Ser Gly Leu
65                  70                  75                  80

Phe Gly Ala Leu Leu Ala Asp Lys Lys Thr Glu Glu Thr Thr Leu Leu
                85                  90                  95

Glu Asp Arg Ile Leu Thr Thr Arg Asn Gly His Thr Thr Ser Thr Thr
            100                 105                 110

Gln Ser Ser Val Gly Val Thr Tyr Gly Tyr Ser Thr Gly Glu Asp His
        115                 120                 125

Val Ser Gly Pro Asn Thr Ser Gly Leu Glu Thr Arg Val Val Gln Ala
    130                 135                 140

Glu Arg Phe Phe Lys Lys His Leu Phe Asp Trp Thr Thr Asp Lys Ala
145                 150                 155                 160

Phe Gly His Leu Glu Lys Leu Glu Leu Pro Thr Glu His Lys Gly Val
                165                 170                 175

Tyr Gly His Leu Val Asp Ser Phe Ala Tyr Met Arg Asn Gly Trp Asp
            180                 185                 190

Val Glu Val Thr Ala Val Gly Asn Gln Phe Asn Gly Gly Cys Leu Leu
        195                 200                 205

Val Ala Met Val Pro Glu Trp Lys Glu Phe Thr Leu Arg Glu Lys Tyr
    210                 215                 220

Gln Leu Thr Leu Phe Pro His Gln Phe Ile Asn Pro Arg Thr Asn Met
225                 230                 235                 240

Thr Ala His Ile Thr Val Pro Tyr Leu Gly Val Asn Arg Tyr Asp Gln
                245                 250                 255

Tyr Lys Gln His Lys Pro Trp Thr Leu Val Val Met Val Val Ser Pro
            260                 265                 270

Leu Thr Thr Ser Ser Ile Gly Ala Ser Gln Ile Lys Val Tyr Ala Asn
        275                 280                 285

Ile Ala Pro Thr Phe Val His Val Ala Gly Glu Leu Pro Ser Lys Glu
    290                 295                 300

Gly Ile Val Pro Val Ala Cys Ser Asp Gly Tyr Gly Gly Leu Val Thr
305                 310                 315                 320

Thr Asp Pro Lys Thr Ala Asp Pro Val Tyr Gly Met Val Tyr Asn Pro
                325                 330                 335

Pro Arg Thr Asn Tyr Pro Gly Arg Phe Thr Asn Leu Leu Asp Val Ala
            340                 345                 350
```

Glu Ala Cys Pro Thr Phe Leu Cys Phe Asp Asp Gly Lys Pro Tyr Val
            355                 360                 365

Val Thr Arg Thr Asp Asp Gln Arg Leu Leu Ala Lys Phe Asp Val Ser
370                 375                 380

Leu Ala Ala Lys His Met Ser Asn Thr Tyr Leu Ser Gly Ile Ala Gln
385                 390                 395                 400

Tyr Tyr Thr Gln Tyr Ser Gly Thr Ile Asn Leu His Phe Met Phe Thr
                405                 410                 415

Gly Ser Thr Glu Ser Lys Ala Arg Tyr Met Val Ala Tyr Ile Pro Pro
            420                 425                 430

Gly Met Asp Thr Pro Pro Asp Thr Pro Glu Lys Ala Ala His Cys Ile
            435                 440                 445

His Ala Glu Trp Asp Thr Gly Leu Asn Ser Lys Phe Thr Phe Ser Ile
450                 455                 460

Pro Tyr Val Ser Ala Ala Asp Tyr Ala Tyr Thr Ala Ser Asp Val Ala
465                 470                 475                 480

Glu Thr Thr Asn Val Gln Gly Trp Val Cys Ile Tyr Gln Ile Thr His
                485                 490                 495

Gly Lys Ala Glu Gln Asp Thr Leu Val Val Ser Val Ser Ala Gly Lys
            500                 505                 510

Asp Phe Glu Leu Arg Leu Pro Ile Asp Pro Arg Thr Gln Thr Thr Thr
            515                 520                 525

Ala Gly Glu Ser Ala Asp Pro Val Thr Thr Val Glu Asn Tyr Gly
530                 535                 540

Gly Glu Thr Gln Ala Gln Arg Gln His Thr Asp Val Gly Phe Ile
545                 550                 555                 560

Met Asp Arg Phe Val Lys Ile Ser Pro Val Ser Pro Thr His Val Ile
                565                 570                 575

Asp Leu Met Gln Thr His Gln His Ala Leu Val Gly Ala Leu Leu Arg
            580                 585                 590

Ala Ala Thr Tyr Tyr Phe Ser Asp Leu Glu Ile Val Val Arg His Asp
            595                 600                 605

Gly Asn Leu Thr Trp Val Pro Asn Gly Ala Pro Val Glu Ala Leu Ala
610                 615                 620

Asn Thr Ser Asn Pro Thr Ala Tyr His Lys Gln Pro Phe Thr Arg Leu
625                 630                 635                 640

Ala Leu Pro Tyr Thr Ala Pro His Arg Val Leu Ala Thr Val Tyr Asn
                645                 650                 655

Gly Val Ser Lys Tyr Ser Thr Thr Gly Asn Gly Arg Arg Gly Asp Leu
            660                 665                 670

Gly Pro Leu Ala Ala Arg Val Ala Ala Gln Leu Pro Ser Ser Phe Asn
            675                 680                 685

Phe Gly Ala Ile Arg Ala Thr Thr Ile His Glu Leu Leu Val Arg Met
690                 695                 700

Lys Arg Ala Glu Leu Tyr Cys Pro Arg Pro Leu Leu Ala Val Glu Val
705                 710                 715                 720

Leu Ser Gln Asp Arg His Lys Gln Lys Ile Ile Ala Pro Thr Lys Gln
                725                 730                 735

Leu Leu Asn Phe Asp Leu Leu Lys Leu Ala Gly Asp Val Glu Ser Asn
            740                 745                 750

Pro Gly Pro Phe Phe Phe Ser Asp Val Arg Thr Asn Phe Ser Lys Leu
            755                 760                 765

-continued

Val Asp Thr Ile Asn Gln Met Gln Glu Asp Met Ser Thr Lys His Gly
770                 775                 780

Pro Asp Phe Asn Arg Leu Val Ser Ala Phe Glu Glu Leu Ala Ala Gly
785                 790                 795                 800

Val Lys Ala Ile Arg Thr Gly Leu Asp Glu Ala Lys Pro Trp Tyr Lys
                805                 810                 815

Leu Ile Lys Leu Leu Ser Arg Leu Ser Cys Met Ala Ala Val Ala Ala
                820                 825                 830

Arg Ser Lys Asp Pro Val Leu Val Ala Ile Met Leu Ala Asp Thr Gly
                835                 840                 845

Leu Glu Ile Leu Asp Ser Thr Phe Val Val Lys Lys Ile Ser Asp Ser
850                 855                 860

Leu Ser Ser Leu Phe His Val Pro Ala Pro Val Phe Ser Phe Gly Ala
865                 870                 875                 880

Pro Ile Leu Leu Ala Gly Leu Val Lys Val Ala Ser Ser Phe Phe Arg
                885                 890                 895

Ser Thr Pro Glu Asp Leu Glu Arg Ala Glu Lys Gln Leu Lys Ala Arg
                900                 905                 910

Asp Ile Ile Glu Arg Gln Lys Pro Leu Lys Val Arg Ala Lys Leu Pro
                915                 920                 925

Gln Gln Glu Gly Pro Tyr Ala Gly Pro Met Glu Arg Gln Lys Pro Leu
930                 935                 940

Lys Val Lys Ala Lys Ala Pro Val Val Lys Glu Gly Pro Tyr Glu Gly
945                 950                 955                 960

Leu Val Lys Lys Pro Val Ala Leu Lys Val Lys Ala Lys Asn Leu Ile
                965                 970                 975

Val Thr Glu Ser Gly Ala Pro Pro Thr Asp Leu Gln Lys Met Val Met
                980                 985                 990

Gly Asn Thr Lys Pro Val Glu Leu Ile Leu Asp Gly Lys Thr Val Ala
                995                 1000                1005

Ile Cys Cys Ala Thr Gly Val Phe Gly Thr Ala Tyr Leu Val Pro
    1010                1015                1020

Arg His Leu Phe Ala Glu Lys Tyr Asp Lys Ile Met Leu Asp Gly
    1025                1030                1035

Arg Ala Met Thr Asp Ser Asp Tyr Arg Val Phe Glu Phe Glu Ile
    1040                1045                1050

Lys Val Lys Gly Gln Asp Met Leu Ser Asp Ala Ala Leu Met Val
    1055                1060                1065

Leu His Arg Gly Asn Arg Val Arg Asp Ile Thr Lys His Phe Arg
    1070                1075                1080

Asp Thr Ala Arg Met Lys Lys Gly Thr Pro Val Val Gly Val Ile
    1085                1090                1095

Asn Asn Ala Asp Val Gly Arg Leu Ile Phe Ser Gly Glu Ala Leu
    1100                1105                1110

Thr Tyr Lys Asp Ile Val Val Cys Met Asp Gly Asp Thr Met Pro
    1115                1120                1125

Gly Leu Phe Ala Tyr Arg Ala Ala Thr Lys Ala Gly Tyr Cys Gly
    1130                1135                1140

Gly Ala Val Leu Ala Lys Asp Gly Ala Glu Thr Phe Ile Val Gly
    1145                1150                1155

Thr His Ser Ala Gly Gly Asn Gly Val Gly Tyr Cys Ser Cys Val
    1160                1165                1170

Ser Arg Ser Met Leu Leu Lys Met Lys Ala His Ile Asp Pro Glu

Pro His His Glu
   1190

<210> SEQ ID NO 7
<211> LENGTH: 3576
<212> TYPE: DNA
<213> ORGANISM: artificial sequence
<220> FEATURE:
<223> OTHER INFORMATION: Polynucleotide encoding Asia FMDV antigen

<400> SEQUENCE: 7

| | | | | | |
|---|---|---|---|---|---|
| atgggagccg | tcaatccag | tccggcaacc | gggtcacaga | accaatctgg | caacactgga | 60 |
| agcatcatta | caactacta | catgcaacag | taccagaatt | ccatggacac | acagcttggt | 120 |
| gacaacgcta | ttagcggagg | ttccaacgaa | ggttccacgg | ataccacttc | cacacacaca | 180 |
| aacaacaccc | aaaacaacga | ctggttctcg | cgcctggcta | gctctgcatt | cagtggtctc | 240 |
| tttggtgcac | ttttggctga | caagaagaca | gaagagacaa | ctctgcttga | agaccgcatt | 300 |
| ctcaccacca | ggaacggcca | cacaacatcg | acgacagt | cgagcgttgg | cgtaacatac | 360 |
| ggttacgctg | tggccgagga | cgcggtgtct | ggacccaata | cctcgggtct | agagactcgt | 420 |
| gttcaacagg | cagaacggtt | tttcaagaaa | cacctgtttg | actggacacc | gaacttggca | 480 |
| tttggacact | gttactacct | ggaacttccc | actgaacaca | aaggcgtgta | cggcagtctc | 540 |
| atgggctcgt | acgcctacat | gagaaatgga | tgggacatag | aggtgactgc | tgttggaaac | 600 |
| caattcaacg | gtggttgtct | ccttgtcgcg | ctcgtgccag | agctgaagga | actcgacacg | 660 |
| cgacagaagt | accagctgac | cctctttccc | caccagttca | tcaacccacg | caccaacatg | 720 |
| acggcccaca | tcaacgtgcc | gtacgtgggt | atcaacaggt | acgaccagta | cgccctccac | 780 |
| aagccgtgga | cgcttgttgt | gatggtggta | gccccactca | ccgtcaaaac | tggtggttct | 840 |
| gaacagatca | aggtttacat | gaatgcagcg | ccaacctacg | tgcatgtggc | gggagagctg | 900 |
| ccctcgaaag | agggaatagt | tcccgtcgcg | tgtgcgacg | gttacggcaa | catggtgacc | 960 |
| acggacccga | gacggccga | tccagtttac | gggaaagtgt | tcaaccccc | caggacaaac | 1020 |
| ctccctgggc | gcttcacgaa | cttccttgat | gttgcgaggg | catgtccaac | tttcctccgc | 1080 |
| tttgagaag | taccattgt | gaagacggtg | aactctggtg | accgcttgct | ggccaagttc | 1140 |
| gacgtgtccc | tcgctgcagg | gcacatgtcc | aacacctact | ggctggcct | ggcgcagtac | 1200 |
| tacacacagt | acagcggcac | catgaacgtc | cacttcatgt | tcaccgggcc | cacggatgct | 1260 |
| aaagcccgat | acatggtggc | ttatgtcccc | cctggcatga | caccgccac | ggaccctgag | 1320 |
| cacgccgcac | actgcattca | ctctgagtgg | atactggtc | ttaactctaa | gtttacctt | 1380 |
| tccataccett | acctctctgc | tgctgactat | gcctacactg | cttctgacgt | ggcggagacc | 1440 |
| acgagtgtgc | agggatgggt | gtgtatctat | cagatcaccc | acggcaaggc | tgagggagac | 1500 |
| gcactggtcg | tttctgtcag | cgccggcaaa | gactttgagt | ttcgcttgcc | tgttgacgca | 1560 |
| cgccagcaaa | ccaccaccac | tggcgaatca | gcagatccag | tcacaaccac | ggttgagaac | 1620 |
| tatgaggag | agactcagac | agccagacgg | cttcacactg | acgtcgcctt | cattcttgac | 1680 |
| aggtttgtga | aactcactgc | tcccaagaac | atccaaaccc | tcgatctcat | gcagatcccc | 1740 |
| tcacacacgc | tggttggagc | actacttcgt | tctgcgacgt | actacttctc | agacctggag | 1800 |
| gtcgcgcttg | tccacacagg | cccggtcacc | tgggtgccca | acggcgcgcc | caaggatgct | 1860 |
| ctaaacaacc | agaccaaccc | aactgcctat | cagaagcaac | ccatcacccg | cctggcactc | 1920 |

-continued

```
ccctacaccg ccccccatcg tgtgctggca acagtgtaca acgggaagac ggcgtacggg      1980
gaaacgacct caaggcgcgg cgacatggcg gccctcgcac aaaggttgag cgctcggctg      2040
cccacctcct tcaactacgg cgccgtgaag gccgacacca tcactgagct tttgatccgc      2100
atgaagcgcg cggagacata ttgccctagg cctttactag cccttgacac cactcaggac      2160
cgccgcaaac aggagatcat tgcacctgag aagcaggttt tgaactttga cctactcaag      2220
ttggcaggag acgttgagtc caaccctggg cccttcttct tctccgacgt taggtcgaac      2280
ttctccaaac tggtcgagac catcaaccag atgcaggagg acatgtcaac aaagcacgga      2340
cccgacttca accggttggt tccgcgtttt gaggaattgg ccacaggagt aaaggccatc      2400
aggaacggtc tcgatgaggc caagccctgg tacaagctca tcaaactcct aagccgcctg      2460
tcgtgcatgg ccgctgtagc agcacggtcc aaggacccag tccttgtggc catcatgctg      2520
gctgacaccg tcttgagat tctggacagc acgttcgtcg tgaagaagat ctccgactcg      2580
ctctccagtc tctttcacgt gccggccccc gtcttcagtt tcggagctcc gattctgttg      2640
gctgggttgg tcaaagtcgc ctcgagtttc ttccggtcca cacccgaaga ccttgagaga      2700
gcagagaaac agctcaaagc acgtgacatc aacgacatac tcgagcgtca gaaacccctg      2760
aaagtgagag ctaagctgcc acaacatgag ggaccttacg ctggcccgat ggagagacag      2820
aaaccactga agtgaaagc aaaagccccg gtcgttaagg aaggaccttta cgagggaccg      2880
gtgaagaagc ctgtcgcttt gaaagtgaaa gctaagaact tgattgtcac tgagagtggt      2940
gccccaccga ccgacttgca aaagatggtc atgagcaaca ctaagcctgt gagctcatc      3000
cttgacggta gacgtggc catctgctgc gccaccggag tgtttggtac tgcctacctc      3060
gtgcctcgtc acctttttcgc agaaaagtac gacaggatca tgttggacgg caggggccatg     3120
acagacagt actacagagt gtttgagttt gagattaaag taaaaggaca ggacatgctc      3180
tcagacgctg cgctcatggt gctccaccgt ggcaaccgtg tgagagacat cacgaaacac      3240
tttcgtgata cagcaagaat gaagaaaggt accccgttg tcggcgtgat caacaacgcc      3300
gacgttggga gactgatttt ctccggtgag gccctcacct acaaggacat tgtagtgtgc      3360
atggatggag acaccatgcc gggcctatt gcctacagag ccgctaccaa ggctggctac      3420
tgtgggaggag ccgttcttgc caaggacgga gctgacacat ttatcgtcgg cactcactcc      3480
gcaggaggca atggagtcgg gtactgctca tgcgtatcta ggtccatgct cttgaagatg      3540
aaggcacaca ttgaccccga accacaccac gagtag                                3576
```

<210> SEQ ID NO 8
<211> LENGTH: 1191
<212> TYPE: PRT
<213> ORGANISM: artificial sequence
<220> FEATURE:
<223> OTHER INFORMATION: Asia FMDV antigen

<400> SEQUENCE: 8

```
Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
            20                  25                  30

Asn Ser Met Asp Thr Gln Leu Gly Asp Asn Ala Ile Ser Gly Gly Ser
        35                  40                  45

Asn Glu Gly Ser Thr Asp Thr Thr Ser Thr His Thr Asn Asn Thr Gln
    50                  55                  60

Asn Asn Asp Trp Phe Ser Arg Leu Ala Ser Ser Ala Phe Ser Gly Leu
```

-continued

```
                65                  70                  75                  80
            Phe Gly Ala Leu Leu Ala Asp Lys Lys Thr Glu Thr Thr Leu Leu
                            85                  90                  95

Glu Asp Arg Ile Leu Thr Thr Arg Asn Gly His Thr Thr Ser Thr Thr
                            100                 105                 110

Gln Ser Ser Val Gly Val Thr Tyr Gly Tyr Ala Val Ala Glu Asp Ala
                            115                 120                 125

Val Ser Gly Pro Asn Thr Ser Gly Leu Glu Thr Arg Val Gln Gln Ala
            130                 135                 140

Glu Arg Phe Phe Lys Lys His Leu Phe Asp Trp Thr Pro Asn Leu Ala
            145                 150                 155                 160

Phe Gly His Cys Tyr Tyr Leu Glu Leu Pro Thr Glu His Lys Gly Val
                            165                 170                 175

Tyr Gly Ser Leu Met Gly Ser Tyr Ala Tyr Met Arg Asn Gly Trp Asp
                            180                 185                 190

Ile Glu Val Thr Ala Val Gly Asn Gln Phe Asn Gly Gly Cys Leu Leu
                            195                 200                 205

Val Ala Leu Val Pro Glu Leu Lys Glu Leu Asp Thr Arg Gln Lys Tyr
            210                 215                 220

Gln Leu Thr Leu Phe Pro His Gln Phe Ile Asn Pro Arg Thr Asn Met
            225                 230                 235                 240

Thr Ala His Ile Asn Val Pro Tyr Val Gly Ile Asn Arg Tyr Asp Gln
                            245                 250                 255

Tyr Ala Leu His Lys Pro Trp Thr Leu Val Val Met Val Val Ala Pro
                            260                 265                 270

Leu Thr Val Lys Thr Gly Gly Ser Glu Gln Ile Lys Val Tyr Met Asn
                            275                 280                 285

Ala Ala Pro Thr Tyr Val His Val Ala Gly Glu Leu Pro Ser Lys Glu
                            290                 295                 300

Gly Ile Val Pro Val Ala Cys Ala Asp Gly Tyr Gly Asn Met Val Thr
            305                 310                 315                 320

Thr Asp Pro Lys Thr Ala Asp Pro Val Tyr Gly Lys Val Phe Asn Pro
                            325                 330                 335

Pro Arg Thr Asn Leu Pro Gly Arg Phe Thr Asn Phe Leu Asp Val Ala
                            340                 345                 350

Glu Ala Cys Pro Thr Phe Leu Arg Phe Gly Val Pro Phe Val Lys
            355                 360                 365

Thr Val Asn Ser Gly Asp Arg Leu Leu Ala Lys Phe Asp Val Ser Leu
            370                 375                 380

Ala Ala Gly His Met Ser Asn Thr Tyr Leu Ala Gly Leu Ala Gln Tyr
            385                 390                 395                 400

Tyr Thr Gln Tyr Ser Gly Thr Met Asn Val His Phe Met Phe Thr Gly
                            405                 410                 415

Pro Thr Asp Ala Lys Ala Arg Tyr Met Val Ala Tyr Val Pro Pro Gly
                            420                 425                 430

Met Thr Pro Pro Thr Asp Pro Glu His Ala Ala His Cys Ile His Ser
                            435                 440                 445

Glu Trp Asp Thr Gly Leu Asn Ser Lys Phe Thr Phe Ser Ile Pro Tyr
                            450                 455                 460

Leu Ser Ala Ala Asp Tyr Ala Tyr Thr Ala Ser Asp Val Ala Glu Thr
            465                 470                 475                 480

Thr Ser Val Gln Gly Trp Val Cys Ile Tyr Gln Ile Thr His Gly Lys
                            485                 490                 495
```

```
Ala Glu Gly Asp Ala Leu Val Val Ser Val Ser Ala Gly Lys Asp Phe
            500                 505                 510
Glu Phe Arg Leu Pro Val Asp Ala Arg Gln Gln Thr Thr Thr Thr Gly
            515                 520                 525
Glu Ser Ala Asp Pro Val Thr Thr Thr Val Glu Asn Tyr Gly Gly Glu
            530                 535                 540
Thr Gln Thr Ala Arg Arg Leu His Thr Asp Val Ala Phe Ile Leu Asp
545                 550                 555                 560
Arg Phe Val Lys Leu Thr Ala Pro Lys Asn Ile Gln Thr Leu Asp Leu
                565                 570                 575
Met Gln Ile Pro Ser His Thr Leu Val Gly Ala Leu Leu Arg Ser Ala
            580                 585                 590
Thr Tyr Tyr Phe Ser Asp Leu Glu Val Ala Leu Val His Thr Gly Pro
            595                 600                 605
Val Thr Trp Val Pro Asn Gly Ala Pro Lys Asp Ala Leu Asn Asn Gln
            610                 615                 620
Thr Asn Pro Thr Ala Tyr Gln Lys Gln Pro Ile Thr Arg Leu Ala Leu
625                 630                 635                 640
Pro Tyr Thr Ala Pro His Arg Val Leu Ala Thr Val Tyr Asn Gly Lys
                645                 650                 655
Thr Ala Tyr Gly Glu Thr Thr Ser Arg Arg Gly Asp Met Ala Ala Leu
            660                 665                 670
Ala Gln Arg Leu Ser Ala Arg Leu Pro Thr Ser Phe Asn Tyr Gly Ala
            675                 680                 685
Val Lys Ala Asp Thr Ile Thr Glu Leu Leu Ile Arg Met Lys Arg Ala
            690                 695                 700
Glu Thr Tyr Cys Pro Arg Pro Leu Leu Ala Leu Asp Thr Thr Gln Asp
705                 710                 715                 720
Arg Arg Lys Gln Glu Ile Ile Ala Pro Glu Lys Gln Val Leu Asn Phe
                725                 730                 735
Asp Leu Leu Lys Leu Ala Gly Asp Val Glu Ser Asn Pro Gly Pro Phe
            740                 745                 750
Phe Phe Ser Asp Val Arg Ser Asn Phe Ser Lys Leu Val Glu Thr Ile
            755                 760                 765
Asn Gln Met Gln Glu Asp Met Ser Thr Lys His Gly Pro Asp Phe Asn
            770                 775                 780
Arg Leu Val Ser Ala Phe Glu Glu Leu Ala Thr Gly Val Lys Ala Ile
785                 790                 795                 800
Arg Asn Gly Leu Asp Glu Ala Lys Pro Trp Tyr Lys Leu Ile Lys Leu
                805                 810                 815
Leu Ser Arg Leu Ser Cys Met Ala Ala Val Ala Ala Arg Ser Lys Asp
            820                 825                 830
Pro Val Leu Val Ala Ile Met Leu Ala Asp Thr Gly Leu Glu Ile Leu
            835                 840                 845
Asp Ser Thr Phe Val Val Lys Lys Ile Ser Asp Ser Leu Ser Ser Leu
            850                 855                 860
Phe His Val Pro Ala Pro Val Phe Ser Phe Gly Ala Pro Ile Leu Leu
865                 870                 875                 880
Ala Gly Leu Val Lys Val Ala Ser Ser Phe Phe Arg Ser Thr Pro Glu
                885                 890                 895
Asp Leu Glu Arg Ala Glu Lys Gln Leu Lys Ala Arg Asp Ile Asn Asp
            900                 905                 910
```

-continued

```
Ile Leu Glu Arg Gln Lys Pro Leu Lys Val Arg Ala Lys Leu Pro Gln
            915                 920                 925

His Glu Gly Pro Tyr Ala Gly Pro Met Glu Arg Gln Lys Pro Leu Lys
    930                 935                 940

Val Lys Ala Lys Ala Pro Val Val Lys Glu Gly Pro Tyr Glu Gly Pro
945                 950                 955                 960

Val Lys Lys Pro Val Ala Leu Lys Val Lys Ala Lys Asn Leu Ile Val
                965                 970                 975

Thr Glu Ser Gly Ala Pro Pro Thr Asp Leu Gln Lys Met Val Met Ser
            980                 985                 990

Asn Thr Lys Pro Val Glu Leu Ile Leu Asp Gly Lys Thr Val Ala Ile
            995                 1000                1005

Cys Cys Ala Thr Gly Val Phe Gly Thr Ala Tyr Leu Val Pro Arg
    1010                1015                1020

His Leu Phe Ala Glu Lys Tyr Asp Arg Ile Met Leu Asp Gly Arg
    1025                1030                1035

Ala Met Thr Asp Ser Asp Tyr Arg Val Phe Glu Phe Glu Ile Lys
    1040                1045                1050

Val Lys Gly Gln Asp Met Leu Ser Asp Ala Ala Leu Met Val Leu
    1055                1060                1065

His Arg Gly Asn Arg Val Arg Asp Ile Thr Lys His Phe Arg Asp
    1070                1075                1080

Thr Ala Arg Met Lys Lys Gly Thr Pro Val Val Gly Val Ile Asn
    1085                1090                1095

Asn Ala Asp Val Gly Arg Leu Ile Phe Ser Gly Glu Ala Leu Thr
    1100                1105                1110

Tyr Lys Asp Ile Val Val Cys Met Asp Gly Asp Thr Met Pro Gly
    1115                1120                1125

Leu Phe Ala Tyr Arg Ala Ala Thr Lys Ala Gly Tyr Cys Gly Gly
    1130                1135                1140

Ala Val Leu Ala Lys Asp Gly Ala Asp Thr Phe Ile Val Gly Thr
    1145                1150                1155

His Ser Ala Gly Gly Asn Gly Val Gly Tyr Cys Ser Cys Val Ser
    1160                1165                1170

Arg Ser Met Leu Leu Lys Met Lys Ala His Ile Asp Pro Glu Pro
    1175                1180                1185

His His Glu
    1190
```

RECOMBINANT ADENOVIRUS VECTORED FMDV VACCINES AND USES THEREOF

CROSS-REFERENCE TO RELATED APPLICATIONS

This application claims priority to U.S. provisional application 62/288,540 filed on Jan. 29, 2016.

This invention was made with Government support. The Government has certain rights in the invention.

FIELD OF THE INVENTION

The present invention relates to compositions for combating Foot and Mouth Disease Virus (FMDV) infection in animals. The present disclosure provides pharmaceutical compositions comprising an FMDV antigen, methods of vaccination against FMDV, and kits for use with such methods and compositions.

BACKGROUND OF THE INVENTION

Foot-and-mouth disease (FMD) is one of the most virulent and contagious diseases affecting farm animals. This disease is endemic in numerous countries in the world, especially in Africa, Asia and South America. In addition, epidemic outbreaks can occur periodically. The presence of this disease in a country may have very severe economic consequences resulting from loss of productivity, loss of weight and milk production in infected herds, and from trade embargoes imposed on these countries. The measures taken against this disease consist of strict application of import restrictions, hygiene controls and quarantine, slaughtering sick animals and vaccination programs using vaccines, either as a preventive measure at the national or regional level, or periodically when an epidemic outbreak occurs.

FMD is characterized by its short incubation period, its highly contagious nature, the formation of ulcers in the mouth and on the feet and sometimes, the death of young animals. FMD affects a number of animal species, in particular cattle, pigs, sheep and goats. The agent responsible for this disease is a ribonucleic acid (RNA) virus belonging to the Aphthovirus genus of the Picornaviridae family (Cooper et al., Intervirology, 1978, 10, 165-180). At present, at least seven types of foot-and-mouth disease virus (FMDV) are known: the European types (A, O and C), the African types (SAT1, SAT2 and SAT3) and an Asiatic type (Asia 1). Numerous sub-types have also been distinguished (Kleid et al. Science (1981), 214, 1125-1129).

FMDV is a naked icosahedral virus of about 25 nm in diameter, containing a single-stranded RNA molecule consisting of about 8500 nucleotides, with a positive polarity. This RNA molecule comprises a single open reading frame (ORF), encoding a single polyprotein containing, inter alia, the capsid precursor also known as protein P1 or P88. Protein P1 is myristylated at its amino-terminal end. During the maturation process, protein P1 is cleaved by protease 3C into three proteins known as VP0, VP1 and VP3 (or 1AB, 1D and 1C respectively; Belsham G. J., Progress in Biophysics and Molecular Biology, 1993, 60, 241-261). In the virion, protein VP0 is then cleaved into two proteins, VP4 and VP2 (or 1A and 1B respectively). The mechanism for the conversion of proteins VP0 into VP4 and VP2, and for the formation of mature virions is not known. Proteins VP1, VP2 and VP3 have a molecular weight of about 26,000 Da, while protein VP4 is smaller at about 8,000 Da.

The simple combination of the capsid proteins forms the protomer or 5S molecule, which is the elementary constituent of the FMDV capsid. This protomer is then complexed into a pentamer to form the 12S molecule. The virion results from the encapsidation of a genomic RNA molecule by assembly of twelve 12S pentamers, thus constituting the 146S particles. The viral capsid may also be formed without the presence of an RNA molecule inside it (hereinafter "empty capsid"). The empty capsid is also designated as particle 70S. The formation of empty capsids may occur naturally during viral replication or may be produced artificially by chemical treatment.

Some studies have been done on natural empty capsids. In particular, Rowlands et al. (Rowlands et al., J. Gen. Virol., 1975, 26, 227-238) have shown that the virions of A10 foot-and-mouth disease comprise mainly the four proteins VP1, VP2, VP3 and VP4. By comparison, the natural empty capsids (not obtained by recombination but purified from cultures of A10 foot-and-mouth virus) essentially contain the uncleaved protein VP0; identical results with the A-Pando foot-and-mouth virus are described by Rweyemamu (Rweyemamu et al., Archives of Virology, 1979, 59, 69-79). The artificial empty capsids, obtained after dialysis in the presence of Tris-EDTA and after centrifuging, contain no protein VP4. These artificial capsids are slightly immunogenic according to Rowlands et al., and the natural empty capsids are only immunogenic after treatment with formaldehyde to stabilize them, while the antibody response induced by the natural empty capsids in the guinea-pig is nevertheless inconstant, as noted by the author. Moreover, Rowlands et al. and Rweyemamu et al. do not agree on the need to stabilize the natural empty capsids. For Rweyemamu et al., the absence of treatment with formaldehyde is not prejudicial to the level of antigenicity of the natural empty capsids. The immunogenicity is only tested by the induction of neutralizing antibodies in the guinea-pig.

The expression of the gene coding for the precursor P1 of the capsid proteins by means of a recombinant baculovirus in insect cells is compared with the expression of the gene coding for P1 associated with the protease 3C in E. coli (Grubman et al., Vaccine, 1993, 11, 825-829; Lewis et al., J. Virol., 1991, 65, 6572-6580). The co-expression of P1 and 3C in E. coli results in the assembling of empty capsids 70S. The expression product of these two constructions produces neutralizing antibodies in guinea-pigs and pigs. The titers obtained with the P1/baculovirus construction are low. These same expression products induce partial protection in pigs. However, some pigs protected against the disease are not protected against the replication of the challenge virus. However, the E. coli expression system does not myristylate the proteins and the protease 3C is toxic to this cell. Lewis et al. conclude that fundamental questions relating to the make-up of the virus and the structure of the capsid needed to obtain maximum protection in the animal have not been answered. Furthermore, Grubman et al. state that it would be necessary to stabilize the empty capsids before formulating the vaccine; on this point they agree about the problems encountered with the empty capsids obtained by extraction from viral cultures (see above).

Fusion proteins containing some or all of protein P1 have also been obtained by the use of viral vectors, namely a herpes virus or vaccinia virus. CA-A-2,047,585 in particular describes a bovine herpes virus used to produce fusion proteins containing a peptide sequence of the foot-and-mouth virus (amino acids 141 to 158 of P1 bound to amino acids 200 to 213 of P1) fused with the glycoprotein gpIII of this bovine herpes virus. Adenovirus vector has been used to express FMDV empty virus capsid (U.S. Pat. No. 8,323, 663). Viral vectors have also been used to express stabilized FMDV empty capsid (U.S. Pat. No. 7,531,182, U.S. Ser. No. 14/863,181). Recently, plants and insect cells have been investigated as a source for the production of FMDV antigens (US 2011/0236416, U.S. Ser. No. 14/863,181).

It has been reported that maternally derived antibodies (MDA) are able to inhibit calves' (under 2 years of age cattle) response to vaccination against FMD (Graves, 1963, Journal of Immunology 91:251-256; Brun et al., 1977, Developments in Biological Standardisation, 25:117-122).

SUMMARY OF THE INVENTION

Compositions or vaccines comprising recombinant viral vectors expressing FMDV polypeptide and fragments and variants thereof are provided. The FMDV antigens and fragments and variants thereof possess immunogenic and protective properties. The recombinant viral vectors may be adenovirus vectors expressing FMDV antigens.

The recombinant viral vectors can be formulated into vaccines and/or pharmaceutical compositions. Such vaccines or compositions can be used to vaccinate an animal and provide protection against homologous and heterologous FMDV strains. The vaccines or compositions formulated with pharmaceutically or veterinarily acceptable carrier, excipient, adjuvant, or vehicle offer thermostability improvements and ability to handle temperature excursions.

Methods for enhanced protection in conventional animals and maternally derived antibody-positive (MDA-positive) animals against FMDV infections are provided. Kits comprising at least one antigenic polypeptide or fragment or variant thereof and instructions for use are also provided.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 1 depicts a table summarizing the DNA and Protein sequences.

FIG. 2 depicts the genes for FMDV A24 strain and the A24 (p1-2AB') genes used in the chimeric A24-A12 construct.

FIG. 3 depicts the genes for FMDV A12 strain and the A12 (3B'/3C) genes used in the chimeric A24-A12 construct.

FIG. 4 depicts the genetic structural identity assay of recombinant adenovirus vectored A24-A12 FMDV vaccine by PCR.

FIG. 5 depicts the western blot of recombinant adenovirus vectored A24-A12 FMDV vaccine.

FIG. 6 depicts the genes for FMDV O1M strain used in the recombinant advenovirus vectored FMDV O1M vaccine.

FIG. 7 depicts the genes for FMDV Irn strain used in the recombinant advenovirus vectored FMDV Irn vaccine.

FIG. 8 depicts the genes for FMDV Asia strain used in the recombinant advenovirus vectored FMDV Asia vaccine.

FIG. 9 depicts the percentage protection by O serotype FMDV vaccine at different doses.

FIG. 10 depicts the serology of O serotype FMDV vaccine at different doses.

FIG. 13 depicts the geometric mean of FMDV VN titer.

FIG. 15 depicts the geometric mean of FMDV VN titer.

DETAILED DESCRIPTION

Figure 11:
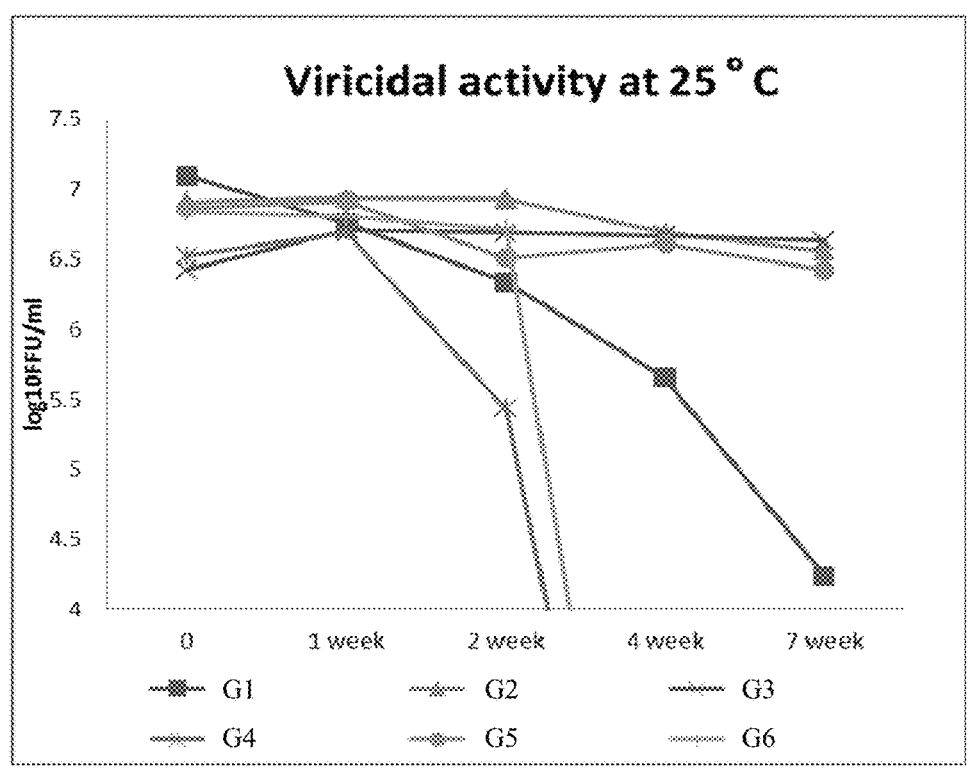
FIG. 11 depicts the viricidal activity of recombinant advenovirus vectored FMDV+adjuvants at 25° C.
Figure 12:
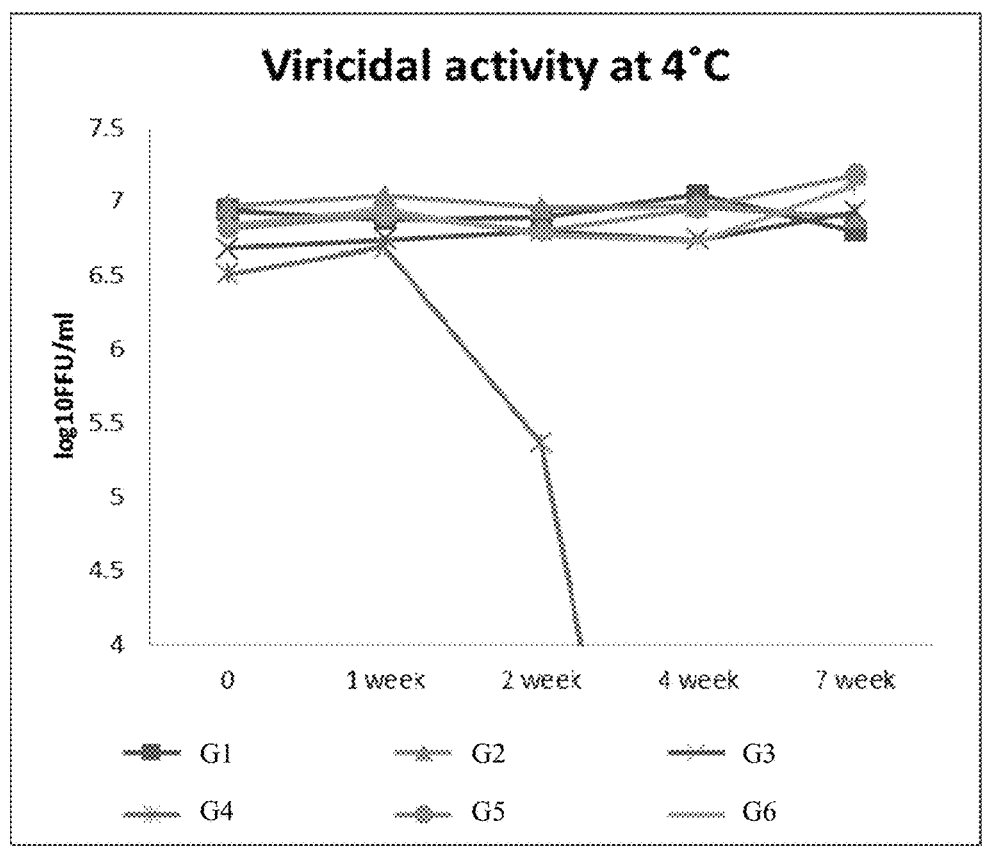
FIG. 12 depicts the viricidal activity of recombinant advenovirus vectored FMDV+adjuvants at 4° C.

Compositions or vaccines comprising recombinant viral vectors expressing FMDV antigens that elicit an immunogenic response in an animal are provided. The recombinant viral vectors may be adenovirus vectors expressing FMDV antigens. The recombinant viral vectors expressing the antigens may be formulated into vaccines or pharmaceutical compositions and used to elicit or stimulate a protective response in an animal. In one embodiment the polypeptide antigen is an FMDV structural protein P1 (VP4-VP2-Vp3-VP1), nonstructural protein P2 (2A, 2B, and 2C) or nonstructural protein P3 (3A, 3B, 3C and 3D) or active fragment or variant thereof.

It is recognized that the antigenic polypeptides of the disclosure may be full length polypeptides or active fragments or variants thereof. By "active fragments" or "active variants" is intended that the fragments or variants retain the antigenic nature of the polypeptide. Thus, the present disclosure encompasses any FMDV polypeptide, antigen, epitope or immunogen that elicits an immunogenic response in an animal. The FMDV polypeptide, antigen, epitope or immunogen may be any FMDV polypeptide, antigen, epitope or immunogen, such as, but not limited to, a protein, peptide or fragment or variant thereof, that elicits, induces or stimulates a response in an animal, such as an ovine, bovine, caprine or porcine.

The simple combination of the capsid proteins forms the protomer or 5S molecule, which is the elementary constituent of the FMDV capsid. This protomer is then complexed into a pentamer to form the 12S molecule. The virion results from the encapsidation of a genomic RNA molecule by assembly of twelve 12S pentamers, thus constituting the 146S particles. The viral capsid may also be formed without the presence of an RNA molecule inside it (hereinafter "empty capsid"). The empty capsid is also designated as particle 70S. The formation of empty capsids may occur naturally during viral replication or may be produced artificially by chemical treatment.

The present disclosure relates to bovine, ovine, caprine, or swine vaccines or compositions which may comprise an effective amount of a recombinant FMDV antigen or a recombinant viral vector expressing FMDV antigen, and a pharmaceutically or veterinarily acceptable carrier, excipient, adjuvant, or vehicle.

In some embodiments, the vaccines further comprise adjuvants, such as the oil-in-water (O/W) emulsions described in U.S. Pat. No. 7,371,395.

In still other embodiments, the adjuvants include TS6, TS7, TS8 and TS9 emulsions, LR3, LR4 and LR6 emulsions, LF2 emulsion, CARBIGEN™ adjuvant, ENABL® adjuvant, polyacrylic acid, aluminum hydroxide or aluminum phosphate, saponin, CpG, water-in-oil emultion, and oil-in-water emulsion, or combinations thereof.

In some embodiments, the response in the animal is a protective immune response.

By "animal" it is intended mammals, birds, and the like. Animal or host includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle, cow), swine (e.g., pig), caprine (e.g., goat), avian (e.g., chicken, duck, goose, turkey, quail, pheasant, parrot, finches, hawk, crow, ostrich, emu and cassowary), primate (e.g., prosimian, tarsier, monkey, gibbon, ape), and fish. The term "animal" also includes an individual animal in all stages of development, including embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

The antigenic polypeptides of the disclosure are capable of protecting against FMDV. That is, they are capable of stimulating an immune response in an animal. By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternatively, the immunogen or antigen may comprise a toxin or antitoxin.

The term "immunogenic protein, polypeptide, or peptide" as used herein includes polypeptides that are immunologically active in the sense that once administered to the host, it is able to evoke an immune response of the humoral and/or cellular type directed against the protein. In embodiments, the protein fragment has substantially the same immunological activity as the total protein. Thus, a protein fragment according to the disclosure can comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques. For example, linear epitopes may be determined by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984, PNAS USA, 81(13): 3998-400; Geysen et al., 1985, PNAS USA, 82(1): 178-82. Similarly, conformational epitopes are readily identified by determining spatial conformation of amino acids such as by, e.g., x-ray crystallography and 2-dimensional nuclear magnetic resonance. Methods especially applicable to the proteins of *T. parva* are described in PCT/US2004/022605.

As discussed the disclosure encompasses active fragments and variants of the antigenic polypeptide. Thus, the term "immunogenic protein, polypeptide, or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence so the encoded amino acid residue does not change or is another biologically similar residue. In this regard, some substitutions will generally be conservative in nature, i.e., those substitutions that take place within a family of amino acids. For example, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response so resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

Synthetic antigens are also included within the definition, for example, polyepitopes, flanking epitopes, and other recombinant or synthetically derived antigens. Immunogenic fragments for purposes of the disclosure will usually include at least about 3 amino acids, at least about 5 amino acids, at least about 10-15 amino acids, or about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides encoding an epitope or antigenic determinant of an FMDV polypeptide. A polynucleotide encoding a fragment of an FMDV polypeptide may comprise or consist essentially of or consist of a minimum of 15 nucleotides, about 30-45 nucleotides, about 45-75, or at least 57, 87 or 150 consecutive or contiguous nucleotides of the sequence encoding the polypeptide.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

The disclosure further comprises a complementary strand to a polynucleotide encoding an FMDV antigen, epitope or immunogen. The complementary strand can be polymeric and of any length, and can contain deoxyribonucleotides, ribonucleotides, and analogs in any combination.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "purified" as used herein does not require absolute purity; rather, it is intended as a relative term. Thus, for example, a purified polypeptide preparation is one in which the polypeptide is more enriched than the polypeptide is in its natural environment. In some instances the polypeptide is separated from cellular components. By "substantially purified" it is intended that so the polypeptide represents several embodiments at least 60%, at least 70%, at least 80%, at least 90%, at least 95%, or at least 98%, or more of the cellular components or materials have been removed. Likewise, the polypeptide may be partially purified. By "partially purified" is intended that less than 60% of the cellular components or material is removed. The same applies to polynucleotides. The polypeptides disclosed herein can be purified by any of the means known in the art.

As noted above, the antigenic polypeptides or fragments or variants thereof are FMDV antigenic polypeptides that are produced by a viral vector in vivo. Fragments and variants of the disclosed polynucleotides and polypeptides encoded thereby are also encompassed by the present disclosure. By "fragment" is intended a portion of the polynucleotide or a portion of the antigenic amino acid sequence encoded thereby. Fragments of a polynucleotide may encode protein fragments that retain the biological activity of the native protein and hence have immunogenic activity as noted elsewhere herein. Fragments of the polypeptide sequence retain the ability to induce a protective immune response in an animal.

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. Variants of a particular polynucleotide of the disclosure (e.g., the reference polynucleotide) can also be evaluated by comparison of the percent sequence identity between the polypeptide encoded by a variant polynucleotide and the polypeptide encoded by the reference polynucleotide. "Variant" protein is intended to mean a protein derived from the native protein by deletion or addition of one or more amino acids at one or more sites in the native protein and/or substitution of one or more amino acids at one or more sites in the native protein. Variant proteins encompassed by the present disclosure are biologically active, that is they the ability to elicit an immune response.

In one aspect, the present disclosure provides FMDV polypeptides from ovine, bovine, caprine, or swine FMDV isolates. In another aspect, the present disclosure provides a polypeptide having a sequence as set forth in SEQ ID NO: 2, 4, 6, or 8, and variant or fragment thereof.

Moreover, homologs of FMDV polypeptides from ovine, bovine, caprine, or swine are intended to be within the scope of the present disclosure. As used herein, the term "homologs" includes orthologs, analogs and paralogs. The term "analogs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type FMDV polypeptide can differ from the wild-type FMDV polypeptide by post-translational modifications, by amino acid sequence differences, or by both. In particular, homologs of the disclosure will generally exhibit at least 80-85%, 85-90%, 90-95%, or 95%, 96%, 97%, 98%, 99% sequence identity, with all or part of the wild-type FMDV polypeptide or polynucleotide sequences, and will exhibit a similar function. Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the disclosure.

As used herein, the term "derivative" or "variant" refers to a polypeptide, or a nucleic acid encoding a polypeptide, that has one or more conservative amino acid variations or other minor modifications so (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the FMDV polypeptide primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein.

The term "conservative variation" denotes the replacement of an amino acid residue by another biologically similar residue, or the replacement of a nucleotide in a nucleic acid sequence so the encoded amino acid residue does not change or is another biologically similar residue. In this regard, particularly preferred substitutions will generally be conservative in nature, as described above.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for FMDV polypeptides, the DNA sequence of the FMDV protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of FMDV protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the FMDV polypeptide encoded by the nucleotide sequence is functionally unchanged.

The sequence identity between two amino acid sequences may be established by the NCBI (National Center for Biotechnology Information) pairwise blast and the blosum62 matrix, using the standard parameters (see, e.g., the BLAST or BLASTX algorithm available on the "National Center for Biotechnology Information" (NCBI, Bethesda, Md., USA) server.

The "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (1983, Proc. Natl. Acad. Sci. USA, vol 80, pp 726-730). The sequence identity or sequence similarity of two amino acid sequences, or the sequence identity between two nucleotide sequences can be determined using Vector NTI software package (Invitrogen, 1600 Faraday Ave., Carlsbad, Calif.). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the disclosure and can be derived from DNA sequences, by thymidine (T) in the DNA sequence being considered equal to uracil (U) in RNA sequences.

Hybridization reactions can be performed under conditions of different "stringency." See for example, "Molecular Cloning: A Laboratory Manual", 4th edition (Sambrook et al., 2014).

The disclosure further encompasses the FMDV polynucleotides contained in a vector molecule or an expression vector and operably linked to a promoter element and optionally to an enhancer.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

The term "recombinant" means a polynucleotide semi-synthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The present disclosure relates to ovine, bovine, caprine and swine vaccines or pharmaceutical or immunological compositions which may comprise an effective amount of a recombinant FMDV antigens and a pharmaceutically or veterinarily acceptable carrier, adjuvant, excipient, or vehicle.

The subject matter described herein is directed in part, to compositions and methods related to the FMDV antigen prepared in a baculovirus/insect cell expression system that is highly immunogenic and protects animals against challenge from homologous and heterologous FMDV strains.

Compositions

The present disclosure relates to FMDV vaccines or compositions which may comprise an effective amount of a recombinant FMDV antigen and a pharmaceutically or veterinarily acceptable carrier, excipient, adjuvant, or vehicle. In one embodiment, the FMDV vaccine or composition comprises a recombinant viral vector expressing FMDV antigens.

One embodiment of the disclosure relates to a vaccine or composition comprising a viral vector expressing FMDV antigens. The FMDV antigens are obtained by expression of the cDNA of regions P1 (VP4-VP2-VP3-VP1), 2A/2B'/3B' and 3C, or P1 (VP4-VP2-VP3-VP1), 2A/2B/2C and 3A/3B/3C/3D. The structural region P1 and the nonstructural regions P2 or P3 may derive from the same FMDV serotype or different serotype (chimeric antigens).

The present disclosure encompasses any FMDV polypeptide, antigen, epitope or immunogen that elicits an immunogenic response in an animal, such as an ovine, bovine, caprine or swine. The FMDV polypeptide, antigen, epitope or immunogen may be any FMDV polypeptide, antigen, epitope or immunogen, such as, but not limited to, a protein, peptide or fragment thereof, that elicits, induces or stimulates a response in an animal, such as an ovine, bovine, caprine or swine.

In an embodiment wherein the FMDV immunological composition or vaccine is a recombinant immunological composition or vaccine, the composition or vaccine comprises a recombinant vector and a pharmaceutical or veterinary acceptable excipient, carrier, adjuvant or vehicle; the recombinant vector is a baculovirus expression vector which may comprise a polynucleotide encoding an FMDV polypeptide, antigen, epitope or immunogen. The FMDV polypeptide, antigen, epitope or immunogen, may be VP1, VP2, VP3, VP4, 2A, 2B, 2C, 3A, 3B, 3C, or 3D, or any combination thereof.

In one embodiment, P1 (VP4-VP2-VP3-VP1)-2A/partial 2B/partial 3B and 3C polypeptides may be expressed in a viral vector and the expression may be regulated by one or more promoter sequences. In another embodiment, the FMDV antigen may be chimeric antigen comprising P1 (VP4-VP2-VP3-VP1)-2A-partial 2B from FMDV serotype A24 and partial 3B from FMDV serotype A12 and 3C antigen from FMDV serotype A24. In yet another embodiment, the FMDV antigen may be P1 (VP4-VP2-VP3-VP1)-2A-2B-partial 2C-partial 3A-3B-3C.

In another embodiment, the FMDV antigen may be derived from FMDV O1 Manisa, O1 BFS or Campos, A24 Cruzeiro, A12, Asia 1 Shamir, A Iran'96, Asia/IRN/05, A22 Iraq, SAT2 Saudi Arabia.

The present disclosure relates to an FMDV vaccine which may comprise an effective amount of a recombinant FMDV antigen or a recombinant viral vector expressing an FMDV antigen, and a pharmaceutically or veterinarily acceptable carrier, excipient, adjuvant, or vehicle.

In another embodiment, pharmaceutically or veterinarily acceptable carrier, excipient, adjuvant, or vehicle may be a water-in-oil emulsion. In yet another embodiment, the pharmaceutically or veterinarily acceptable carrier, excipient, adjuvant, or vehicle may be an oil-in-water emulsion.

The disclosure further encompasses the FMDV polynucleotides contained in a vector molecule or an expression vector and operably linked to a promoter element and optionally to an enhancer.

In one aspect, the present disclosure provides FMDV polypeptides, particularly ovine, bovine, caprine or swine polypeptides having a sequence as set forth in SEQ ID NO: 2, 4, 6, or 8, and variants or fragments thereof.

In another aspect, the present disclosure provides a polypeptide having at least 70%, at least 75%, at least 80%, at least 85%, at least 90%, at least 95%, 96%, 97%, 98% or 99% sequence identity to an antigenic polypeptide of the disclosure, particularly to the polypeptides having a sequence as set forth in SEQ ID NO: 2, 4, 6, or 8.

In yet another aspect, the present disclosure provides fragments and variants of the FMDV polypeptides identified above (SEQ ID NO: 2, 4, 6, or 8) which may readily be prepared by one of skill in the art using molecular biology techniques.

Variants are homologous polypeptides having an amino acid sequence at least 75%, 80%, 85%, 90%, 95%, 96%, 97%, 98%, or 99% identity to the amino acid sequence as set forth in SEQ ID NO: 2, 4, 6, or 8.

An immunogenic fragment of an FMDV polypeptide includes at least 8, 10, 15, or 20 consecutive amino acids, at least 21 amino acids, at least 23 amino acids, at least 25 amino acids, or at least 30 amino acids of an FMDV polypeptide having a sequence as set forth in SEQ ID NO: 2, 4, 6, or 8, or variants thereof. In another embodiment, a fragment of an FMDV polypeptide includes a specific antigenic epitope found on a full-length FMDV polypeptide.

In another aspect, the present disclosure provides a polynucleotide encoding an FMDV polypeptide, such as a polynucleotide encoding a polypeptide having a sequence as set forth in SEQ ID NO: 2, 4, 6, or 8. In yet another aspect, the present disclosure provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 2, 4, 6, or 8, or a conservative variant, an allelic variant, a homolog or an immunogenic fragment comprising at least eight or at least ten consecutive amino acids of one of these polypeptides, or a combination of these polypeptides.

In another aspect, the present disclosure provides a polynucleotide having a nucleotide sequence as set forth in SEQ ID NO:1, 3, 5, or 7, or a variant thereof. In yet another aspect, the present disclosure provides a polynucleotide having at least 70%, at least 75%, at least 80%, at least 85%, at least 90%, at least 95%, at least 95%, 96%, 97%, 98%, or 99% sequence identity to one of a polynucleotide having a sequence as set forth in SEQ ID NO: 1, 3, 5, or 7, or a variant thereof.

The polynucleotides of the disclosure may comprise additional sequences, such as additional encoding sequences within the same transcription unit, controlling elements such as promoters, ribosome binding sites, enhancer, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this disclosure.

Elements for the expression of an FMDV polypeptide, antigen, epitope or immunogen are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a polyprotein fragment, e.g., an FMDV peptide, advantageously, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

The present disclosure also relates to preparations comprising vectors, such as expression vectors, e.g., therapeutic compositions. The preparations can comprise one or more vectors, e.g., expression vectors, such as in vivo expression vectors, comprising and expressing one or more FMDV polypeptides, antigens, epitopes or immunogens. In one embodiment, the vector contains and expresses a polynucleotide that comprises, consists essentially of, or consists of a polynucleotide coding for (and advantageously expressing) an FMDV antigen, epitope or immunogen, in a pharmaceutically or veterinarily acceptable carrier, excipient or vehicle. Thus, according to an embodiment of the disclosure, the other vector or vectors in the preparation comprises, consists essentially of or consists of a polynucleotide that encodes, and under appropriate circumstances the vector expresses one or more other proteins of an FMDV polypeptide, antigen, epitope or immunogen, or a fragment thereof.

According to another embodiment, the vector or vectors in the preparation comprise, or consist essentially of, or consist of polynucleotide(s) encoding one or more proteins or fragment(s) thereof of an FMDV polypeptide, antigen, epitope or immunogen, the vector or vectors expressing the polynucleotide(s). In another embodiment, the preparation comprises one, two, or more vectors comprising polynucleotides encoding and expressing, advantageously in vivo, an FMDV polypeptide, antigen, fusion protein or an epitope thereof. The disclosure is also directed at mixtures of vectors that comprise polynucleotides encoding and expressing different FMDV polypeptides, antigens, epitopes or immunogens, e.g., an FMDV polypeptide, antigen, epitope or immunogen from different animal species such as, but not limited to, ovine, bovine, caprine or swine.

According to a yet further embodiment of the disclosure, the expression vector is a plasmid vector or a DNA plasmid vector, in particular an in vivo expression vector. In a specific, non-limiting example, the pVR1020 or 1012 plasmid (VICAL, Inc.; Luke et al., 1997; Hartikka et al., 1996, Hum Gene Ther, 7(10): 1205-17; see, e.g., U.S. Pat. Nos. 5,846,946 and 6,451,769) can be utilized as a vector for the insertion of a polynucleotide sequence. The pVR1020 plasmid is derived from pVR1012 and contains the human tPA signal sequence. In an embodiment, the human tPA signal comprises from amino acid M(1) to amino acid S(23) in Genbank under the accession number HUMTPA14. In another specific, non-limiting example, the plasmid utilized as a vector for the insertion of a polynucleotide sequence can contain the signal peptide sequence of equine IGF1 from amino acid M(24) to amino acid A(48) in Genbank under the accession number U28070. Additional information on DNA plasmids which may be consulted or employed in the practice are found, for example, in U.S. Pat. Nos. 6,852,705; 6,818,628; 6,586,412; 6,576,243; 6,558,674; 6,464,984; 6,451,770; 6,376,473; and 6,221,362.

The term plasmid covers any DNA transcription unit comprising a polynucleotide according to the disclosure and the elements necessary for its in vivo expression in a cell or cells of the desired host or target; and, in this regard, it is noted that a supercoiled or non-supercoiled, circular plasmid, as well as a linear form, are intended to be within the scope of the disclosure.

A plasmid can comprises or contains or consists essentially of, in addition to the polynucleotide encoding an FMDV antigen, epitope or immunogen, optionally fused with a heterologous peptide sequence, variant, analog or fragment, operably linked to a promoter or under the control of a promoter or dependent upon a promoter. In general, it is advantageous to employ a strong promoter functional in eukaryotic cells. The strong promoter may be, but not limited to, the immediate early cytomegalovirus promoter (CMV-IE) of human or murine origin, or optionally having another origin such as the rat or guinea pig, the Super promoter (Ni, M. et al., Plant J. 7, 661-676, 1995.). The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4, 968,615, as well as to PCT Application No WO87/03905. In embodiments, the CMV-IE promoter is a human CMV-IE (Boshart et al., 1985, Cell, 41(2): 521-30) or murine CMV-IE.

In more general terms, the promoter is of a viral, a plant, or a cellular origin. A strong viral promoter other than CMV-IE that may be employed in the practice of the disclosure is the early/late promoter of the SV40 virus or the LTR promoter of the Rous sarcoma virus. A strong cellular promoter that may be usefully employed in the practice of the disclosure is the promoter of a gene of the cytoskeleton, such as, e.g., the desmin promoter (Kwissa et al., 2000, Vaccine, 18(22): 2337-44), or the actin promoter (Miyazaki et al., 1989, Gene, 79(2): 269-77).

The plasmids may comprise other expression control elements. It is particularly advantageous to incorporate stabilizing sequence(s), e.g., intron sequence(s), for example, maize alcohol dehydrogenase intron (Callis et al. Genes & Dev. 1(10):1183-1200, December 1987), the first intron of the hCMV-IE (PCT Application No. WO1989/01036), the intron II of the rabbit β-globin gene (van Ooyen et al., 1979, Science, 206(4416): 337-44). In another embodiment, the plasmids may comprise 3' UTR. The 3' UTR may be, but not limited to, *agrobacterium* nopaline synthase (Nos) 3' UTR (Nopaline synthase: transcript mapping and DNA sequence. Depicker, A. et al. J. Mol. Appl. Genet., 1982; Bevan, N A R, 1984, 12(22): 8711-8721).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

In one embodiment, the recombinant FMDV antigen is expressed in insect cells.

Methods of Use

In an embodiment, the subject matter disclosed herein is directed to a method of vaccinating an ovine, bovine, caprine, or swine comprising administering to the ovine, bovine, caprine, or swine an effective amount of a vaccine which may comprise a recombinant viral vector expressing an FMDV antigen, and a pharmaceutically or veterinarily acceptable carrier, excipient, adjuvant, or vehicle.

In one embodiment of the present disclosure, the method comprises a single administration of a vaccine composition formulated with an emulsion according to the disclosure. For example, in one embodiment, the immunological or vaccine composition comprises a recombinant viral vector expressing an FMDV antigen.

In another embodiment of the present disclosure, the method comprises a single administration of two heterologous vaccine compositions. The heterologous vaccines or compositions may be different types of vaccines, such as FMDV VLPs vaccine or FMDV viral vector vaccines. The heterologous vaccines may also be the same type of vaccines expressing the capsids of different FMDV serotypes, such as A24, A12, O1 Manisa, Asia or Iraq strains.

In an embodiment, the subject matter disclosed herein is directed to a method of vaccinating an ovine, bovine, caprine, or swine comprising administering to the ovine, bovine, caprine, or swine a vaccine comprising a recombinant viral vector expressing an FMDV antigen in vivo.

In an embodiment, the subject matter disclosed herein is directed to a method of eliciting an immune response comprising administering to the ovine, bovine, caprine, or swine a vaccine comprising a recombinant viral vector expressing an FMDV antigen in vivo.

Both homologous and heterologous FMDV strains are used for challenge to test the efficacy of the vaccine. The administering may be subcutaneously or intramuscularly. The administering may be needle free (for example Pigjet or Bioject).

In one embodiment of the disclosure, a prime-boost regimen can be employed, which is comprised of at least one primary administration and at least one booster administration using at least one common polypeptide, antigen, epitope or immunogen. The immunological composition or vaccine used in primary administration is different in nature from those used as a booster. However, it is noted that the same composition can be used as the primary administration and the boost. This administration protocol is called "prime-boost".

A prime-boost according to the present disclosure can include a recombinant viral vector that is used to express an FMDV coding sequence or fragments thereof encoding an antigenic polypeptide or fragment or variant thereof. Specifically, the viral vector can express an FMDV gene or fragment thereof that encodes an antigenic polypeptide. Viral vector contemplated herein includes, but not limited to, poxvirus [e.g., vaccinia virus or attenuated vaccinia virus, avipox virus or attenuated avipox virus (e.g., canarypox, fowlpox, dovepox, pigeonpox, quailpox, ALVAC, TROVAC; see e.g., U.S. Pat. Nos. 5,505,941 and 5,494,807), raccoonpox virus, swinepox virus, etc.], adenovirus (e.g., human adenovirus, canine adenovirus), herpesvirus (e.g. canine herpesvirus, herpesvirus of turkey, Marek's disease virus, infectious laryngotracheitis virus, feline herpesvirus, laryngotracheitis virus (ILTV), bovine herpesvirus, swine herpesvirus), baculovirus, retrovirus, etc. In another embodiment, the avipox expression vector may be a canarypox vector, such as, ALVAC. In yet another embodiment, the avipox expression vector may be a fowlpox vector, such as, TROVAC. The FMDV antigen of the disclosure to be expressed is inserted under the control of a specific poxvirus promoter, e.g., the entomopoxvirus *Amsacta moorei* 42K promoter (Barcena, Lorenzo et al., 2000, J Gen Virol., 81(4): 1073-85), the vaccinia promoter 7.5 kDa (Cochran et al., 1985, J Virol, 54(1): 30-7), the vaccinia promoter I3L (Riviere et al., 1992, J Virol, 66(6): 3424-34), the vaccinia promoter HA (Shida, 1986, Virology, 150(2): 451-62), the cowpox promoter ATI (Funahashi et al., 1988, J Gen Virol, 69 (1): 35-47), the vaccinia promoter H6 (Taylor et al., 1988, Vaccine, 6(6): 504-8; Guo et al., 1989, J Virol, 63(10): 4189-98; Perkus et al., 1989, J Virol, 63(9): 3829-36.), inter alia.

In another embodiment, the avipox expression vector may be a canarypox vector, such as, ALVAC. The FMDV antigen, epitope or immunogen may be FMDV P1-3C. The FMDV viral vector may be a canarypox virus such as vCP2186, vCP2181, or vCP2176, or a fowlpox virus such as vFP2215 (see U.S. Pat. No. 7,527,960). In yet another embodiment, the FMDV antigen, epitope or immunogen may be produced in duckweed (U.S. Published Patent Application 2011/0236416).

In another aspect of the prime-boost protocol of the disclosure, a composition comprising the FMDV antigen of the disclosure is administered followed by the administration of vaccine or composition comprising a subunit vaccine comprising FMDV VLPs expressed by baculovirus in insect cells (see U.S. Ser. No. 14/863,181), or an inactivated viral vaccine or composition comprising the FMDV antigen, or a DNA plasmid vaccine or composition that contains or expresses the FMDV antigen. Likewise, a prime-boost protocol may comprise the administration of vaccine or composition comprising a subunit vaccine comprising FMDV VLPs expressed by baculovirus in insect cells, or an inactivated viral vaccine or composition comprising an FMDV antigen, or a DNA plasmid vaccine or composition that contains or expresses an FMDV antigen, followed by the administration of a composition comprising the FMDV antigen of the disclosure. It is further noted that both the primary and the secondary administrations may comprise the composition comprising the FMDV antigen of the disclosure.

A prime-boost protocol comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations.

The dose volume of compositions for target species that are mammals, e.g., the dose volume of ovine, bovine, caprine or swine compositions, based on viral vectors, e.g., non-poxvirus-viral-vector-based compositions, is generally between about 0.1 to about 5.0 ml, between about 0.1 to about 3.0 ml, and between about 0.5 ml to about 2.5 ml.

The efficacy of the vaccines may be tested about 2 to 4 weeks after the last immunization by challenging animals, such as ovine, bovine, caprine or swine, with a virulent strain of FMDV, such as the FMDV O1 Manisa, O1 BFS or Campos, A24 Cruzeiro, A12, Asia 1 Shamir, A Iran '96, Asia/IRN/05, A22 Iraq, SAT2 Saudi Arabia strains.

Still other strains may include FMDV strains A10-61, A5, A12, A24/Cruzeiro, C3/Indaial, O1, C1-Santa Pau, C1-C5, A22/550/Azerbaijan/65, SAT1-SAT3, A, A/TNC/71/94, A/IND/2/68, A/IND/3/77, A/IND/5/68, A/IND/7/82, A/IND/16/82, A/IND/17/77, A/IND/17/82, A/IND/19/76, A/IND/20/82, A/IND/22/82, A/IND/25/81, A/IND/26/82, A/IND/54/79, A/IND/57/79, A/IND/73/79, A/IND/85/79, A/IND/86/79, A/APA/25/84, A/APN/41/84, A/APS/44/05, A/APS/50/05, A/APS/55/05, A/APS/66/05, A/APS/68/05, A/BIM/46/95, A/GUM/33/84, A/ORS/66/84, A/ORS/75/88, A/TNAn/60/947/Asia/1, A/IRN/05, Asia/IRN/05, O/HK/2001, O/UKG/3952/2001, O/UKG/4141/2001, Asia 1/HNK/CHA/05 (GenBank accession number EF149010, herein incorporated by reference), Asia I/XJ (Li, ZhiYong et al. Chin Sci Bull, 2007), HK/70 (Chin Sci Bull, 2006, 51(17): 2072-2078), O/UKG/7039/2001, O/UKG/9161/2001, O/UKG/7299/2001, O/UKG/4014/2001, O/UKG/4998/2001, O/UKG/9443/2001, O/UKG/5470/2001, O/UKG/

5681/2001, O/ES/2001, HKN/2002, O5India, O/BKF/2/92, K/37/84/A, KEN/1/76/A, GAM/51/98/A, A10/Holland, O/KEN/1/91, O/IND49/97, O/IND65/98, O/IND64/98, O/IND48/98, O/IND47/98, O/IND82/97, O/IND81/99, O/IND81/98, O/IND79/97, O/IND78/97, O/IND75/97, O/IND74/97, O/IND70/97, O/IND66/98, O/IND63/97, O/IND61/97, O/IND57/98, O/IND56/98, O/IND55/98, O/IND54/98, O/IND469/98, O/IND465/97, O/IND464/97, O/IND424/97, O/IND423/97, O/IND420/97, O/IND414/97, O/IND411/97, O/IND410/97, O/IND409/97, O/IND407/97, O/IND399/97, O/IND39/97, O/IND391/97, O/IND38/97, O/IND384/97, O/IND380/97, O/IND37/97, O/IND352/97, O/IND33/97, O/IND31/97, O/IND296/97, O/IND23/99, O/IND463/97, O/IND461/97, O/IND427/98, O/IND28/97, O/IND287/99, O/IND285/99, O/IND282/99, O/IND281/97, O/IND27/97, O/IND278/97, O/IND256/99, O/IND249/99, O/IND210/99, O/IND208/99, O/IND207/99, O/IND205/99, O/IND185/99, O/IND175/99, O/IND170/97, O/IND164/99, O/IND160/99, O/IND153/99, O/IND148/99, O/IND146/99, O/SKR/2000, A22/India/17/77.

Further details of these FMDV strains may be found on the European Bioinformatics Information (EMBL-EBI) web pages, and all of the associated nucleotide sequences are herein incorporated by reference. The inventors contemplate that all FMDV strains, both herein listed, and those yet to be identified, could be expressed according to the teachings of the present disclosure to produce, for example, effective vaccine compositions. Both homologous and heterologous strains are used for challenge to test the efficacy of the vaccines. The animal may be challenged intradermally, subcutaneously, spray, intra-nasally, intra-ocularly, intra-tracheally, and/or orally.

The prime-boost administrations may be advantageously carried out 1 to 6 weeks apart, for example, about 3 weeks apart. According to one embodiment, a semi-annual booster or an annual booster, advantageously using the viral vector-based vaccine, is also envisaged. The animals are advantageously at least 6 to 8 weeks old or about 6 months old at the time of the first administration.

The compositions comprising the recombinant antigenic polypeptides of the disclosure used in the prime-boost protocols are contained in a pharmaceutically or veterinary acceptable vehicle, diluent, adjuvant, or excipient. The protocols of the disclosure protect the animal from ovine, bovine, caprine or porcine FMDV and/or prevent disease progression in an infected animal.

It should be understood by one of skill in the art that the disclosure herein is provided by way of example and the present disclosure is not limited thereto. From the disclosure herein and the knowledge in the art, the skilled artisan can determine the number of administrations, the administration route, and the doses to be used for each injection protocol, without any undue experimentation.

The present disclosure contemplates at least one administration to an animal of an efficient amount of the therapeutic composition made according to the disclosure. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the disclosure can also be administered by a needleless apparatus (as, for example with a Pigjet, Dermojet, Biojector, Avijet (Merial, Ga., USA), Vetj et or Vitajet apparatus (Bioject, Oreg., USA)). Another approach to administering plasmid compositions is to use electroporation (see, e.g. Tollefsen et al., 2002; Tollefsen et al., 2003; Babiuk et al., 2002; PCT Application No. WO99/01158). In another embodiment, the therapeutic composition is delivered to the animal by gene gun or gold particle bombardment.

In one embodiment, the disclosure provides for the administration of a therapeutically effective amount of a formulation for the delivery and expression of an FMDV antigen or epitope in a target cell. Determination of the therapeutically effective amount is routine experimentation for one of ordinary skill in the art. In one embodiment, the formulation comprises an expression vector comprising a polynucleotide that expresses an FMDV antigen or epitope and a pharmaceutically or veterinarily acceptable carrier, vehicle or excipient. In another embodiment, the pharmaceutically or veterinarily acceptable carrier, vehicle or excipient facilitates transfection or other means of transfer of polynucleotides to a host animal and/or improves preservation of the vector or protein in a host.

In one embodiment, the subject matter disclosed herein provides a detection method for differentiation between infected and vaccinated animals (DIVA).

It is disclosed herein that the use of the vaccine or composition of the present disclosure allows the detection of FMDV infection in an animal. It is disclosed herein that the use of the vaccine or composition of the present disclosure allows the detection of the infection in animals by differentiating between infected and vaccinated animals (DIVA). Methods are disclosed herein for diagnosing the infection of FMDV in an animal using an FMDV non-structural protein (e.g., a FMDV 3ABC or 3D-specific ELISA).

Article of Manufacture

In an embodiment, the subject matter disclosed herein is directed to a kit for performing a method of eliciting or inducing an immune response which may comprise any one of the recombinant FMDV immunological compositions or vaccines, or inactivated FMDV immunological compositions or vaccines, recombinant FMDV viral compositions or vaccines, and instructions for performing the method.

Another embodiment of the disclosure is a kit for performing a method of inducing an immunological or protective response against FMDV in an animal comprising a composition or vaccine comprising an FMDV antigen of the disclosure and a recombinant FMDV viral immunological composition or vaccine, and instructions for performing the method of delivery in an effective amount for eliciting an immune response in the animal.

Another embodiment of the disclosure is a kit for performing a method of inducing an immunological or protective response against FMDV in an animal comprising a composition or vaccine comprising an FMDV antigen of the disclosure and an inactivated FMDV immunological composition or vaccine, and instructions for performing the method of delivery in an effective amount for eliciting an immune response in the animal.

Yet another aspect of the present disclosure relates to a kit for prime-boost vaccination according to the present disclosure as described above. The kit may comprise at least two vials: a first vial containing a vaccine or composition for the prime-vaccination according to the present disclosure, and a second vial containing a vaccine or composition for the boost-vaccination according to the present disclosure. The kit may contain additional first or second vials for additional prime-vaccinations or additional boost-vaccinations.

In an embodiment, a composition comprising an FMDV antigen or fragment or variant thereof and a pharmaceutically or veterinarily acceptable carrier, excipient, adjuvant, or vehicle is disclosed. In another embodiment, a composition comprising a recombinant viral vector expressing FMDV antigens and a pharmaceutically or veterinarily acceptable carrier, excipient, adjuvant, or vehicle is disclosed. In another embodiment, the composition described above wherein the FMDV antigen or fragment or variant thereof comprises an immunogenic fragment comprising at least 15 amino acids of an ovine, bovine, caprine, or swine FMDV antigen is disclosed. In an embodiment, the above compositions wherein the FMDV antigen or fragment or variant thereof is partially purified are disclosed. In an embodiment, the above compositions wherein the FMDV antigen or fragment or variant thereof is substantially purified are disclosed.

In an embodiment, the above compositions wherein the FMDV antigen or fragment or variant thereof is an ovine, bovine, caprine, or swine FMDV polypeptide are disclosed. In an embodiment, the above compositions wherein the FMDV polypeptide is a P1 polypeptide, VP0 polypeptide, VP1 polypeptide, VP3 polypeptide, VP2 polypeptide, VP4 polypeptide, 2A polypeptide, 2B polypeptide, 2C polypeptide, 3A polypeptide, 3B polypeptide, 3C polypeptide, or 3D polypeptide are disclosed. In an embodiment, the above compositions wherein the FMDV antigen or fragment or variant thereof has at least 80% sequence identity to the sequence as set forth in SEQ ID NO: 2, 4, 6, or 8 are disclosed. In one embodiment, the above compositions wherein the FMDV antigen is encoded by a polynucleotide having at least 70% sequence identity to the sequence as set forth in SEQ ID NO: 1, 3, 5, or 7 are disclosed. In an embodiment, the above compositions wherein the pharmaceutically or veterinarily acceptable carrier, excipient, adjuvant, or vehicle is a water-in-oil emulsion or an oil-in-water emulsion are disclosed. In another embodiment, a method of vaccinating an animal susceptible to ovine, bovine, caprine, or swine FMDV comprising administering the compositions above to the animal is disclosed. In an embodiment, a method of vaccinating an animal susceptible to ovine, bovine, caprine, or swine FMDV comprising a prime-boost regimen is disclosed. In an embodiment, a substantially purified antigenic polypeptide expressed in insect cells, wherein the polypeptide comprises: an amino acid sequence having at least 80% sequence identity to a polypeptide having the sequence as set forth in SEQ ID NO: 2, 4, 6, or 8 is disclosed. In any embodiment the animal is preferably an ovine, a bovine, a swine, or a caprine. In one embodiment, a method of diagnosing FMDV infection in an animal is disclosed. In yet another embodiment, a kit for prime-boost vaccination comprising at least two vials, wherein a first vial containing the composition comprising an FMDV antigen or fragment or variant thereof, and a second vial containing a recombinant viral vector that contains or expresses the FMDV antigen is disclosed.

The pharmaceutically or veterinarily acceptable carriers or vehicles or adjuvants or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this disclosure include, but are not limited to, poly-(L-glutamate) or polyvinylpyrrolidone. The pharmaceutically or veterinarily acceptable carrier or vehicle or adjuvants or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

$$R_1-O-CH_2-CH-CH_2-\overset{+}{\underset{CH_3}{\overset{CH_3}{N}}}-R_2-X$$
$$\phantom{R_1-O-CH_2-}OR_1$$

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr, 1994), to form DMRIE-DOPE.

Advantageously, the plasmid mixture with the adjuvant is formed extemporaneously and advantageously contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is about 95:about 5 to about 5:about 95, more advantageously about 1:about 1, e.g., 1:1.

The DMRIE or DMRIE-DOPE adjuvant:plasmid weight ratio can be between about 50:about 1 and about 1:about 10, such as about 10:about 1 and about 1:about 5, and about 1:about 1 and about 1:about 2, e.g., 1:1 and 1:2.

In another embodiment, pharmaceutically or veterinarily acceptable carrier, excipient, adjuvant, or vehicle may be a water-in-oil emulsion. Examples of suitable water-in-oil emulsions include oil-based water-in-oil vaccinal emulsions which are stable and fluid at 4° C. containing: from 6 to 50 v/v % of an antigen-containing aqueous phase, preferably from 12 to 25 v/v %, from 50 to 94 v/v % of an oil phase containing in total or in part a non-metabolizable oil (e.g., mineral oil such as paraffin oil) and/or metabolizable oil (e.g., vegetable oil, or fatty acid, polyol or alcohol esters), from 0.2 to 20 p/v % of surfactants, preferably from 3 to 8 p/v %, the latter being in total or in part, or in a mixture either polyglycerol esters, said polyglycerol esters being preferably polyglycerol (poly)ricinoleates, or polyoxyethylene ricin oils or else hydrogenated polyoxyethylene ricin oils. Examples of surfactants that may be used in a water-in-oil emulsion include ethoxylated sorbitan esters (e.g., polyoxyethylene (20) sorbitan monooleate (TWEEN 80®), available from AppliChem, Inc., Cheshire, Conn.) and sorbitan esters (e.g., sorbitan monooleate (SPAN 80®), available from Sigma Aldrich, St. Louis, Mo.). In addition, with respect to a water-in-oil emulsion, see also U.S. Pat. No. 6,919,084, e.g., Example 8 thereof, incorporated herein by reference. In some embodiments, the antigen-containing aqueous phase comprises a saline solution comprising one or more buffering agents. An example of a suitable buffering solution is phosphate buffered saline. In an advantageous embodiment, the water-in-oil emulsion may be a water/oil/water (W/O/W) triple emulsion (U.S. Pat. No. 6,358,500). Examples of other suitable emulsions are described in U.S. Pat. No. 7,371,395.

The immunological compositions and vaccines according to the disclosure may comprise or consist essentially of one or more adjuvants. Suitable adjuvants for use in the practice of the present disclosure are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996, PNAS USA, 93(7): 2879-83; WO98/16247), (3) an oil in water emulsion, such as the SPT emulsion described on page 147 of "Vaccine Design, The Subunit and Adjuvant Approach" published by M. Powell, M. Newman, Plenum Press 1995, 6: 147, 183, and the emulsion MF59 described on page 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name CARBOPOL® (BF Goodrich, Ohio, USA) are especially suitable. They are crosslinked by allyl saccharose or by allyl pentaerythritol. Among them, reference is made to CARBOPOL® 1 974P, 934P and 971P.

As to the maleic anhydride-alkenyl derivative copolymers, preference is given to EMA® (Monsanto), which are straight-chain or crosslinked ethylene-maleic anhydride copolymers and they are, for example, crosslinked by divinyl ether.

With regard to structure, the acrylic or methacrylic acid polymers and EMA® are preferably formed by basic units having the following formula:

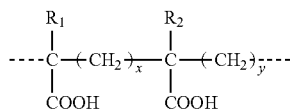

in which:
R1 and R2, which can be the same or different, represent H or CH3
x=0 or 1, preferably x=1
y=1 or 2, with x+y=2.
For EMA®, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final immunological or vaccine composition can range between about 0.01 to about 1.5% w/v, about 0.05 to about 1% w/v, and about 0.1 to about 0.4% w/v.

The cytokine or cytokines (5) can be in protein form in the immunological or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector thereof.

The disclosure comprehends preparing such combination compositions; for instance by admixing the active components, advantageously together and with an adjuvant, carrier, cytokine, and/or diluent.

Cytokines that may be used in the present disclosure include, but are not limited to, granulocyte colony stimulating factor (G-CSF), granulocyte/macrophage colony stimulating factor (GM-CSF), interferon α (IFNα), interferon β (IFNβ), interferon γ, (IFNγ), interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNFα), tumor necrosis factor β (TNFβ), polyinosinic and polycytidylic acid, cytidine-phosphate-guanosine oligodeoxynucleotides (CpG ODN), and transforming growth factor β (TGFβ). It is understood that cytokines can be co-administered and/or sequentially administered with the immunological or vaccine composition of the present disclosure. Thus, for instance, the vaccine of the instant disclosure can also contain an exogenous nucleic acid molecule that expresses in vivo a suitable cytokine, e.g., a cytokine matched to this host to be vaccinated or in which an immunological response is to be elicited (for instance, a bovine cytokine for preparations to be administered to bovines).

In a particular embodiment, the adjuvant may include TS6, TS7, TS8 and TS9 emulsions (U.S. Pat. No. 7,371, 395); LR3 and LR4 (U.S. Pat. No. 7,691,368); TSAP (U.S. Published Patent Application 20110129494); TRIGEN™ (Newport Labs); synthetic dsRNAs (e.g. poly-IC, poly-ICLC [HILTONOL®]); CARBIGEN™ adjuvant (MVP Laboratories, Inc.); ENABL® adjuvant (VaxLiant); and MONTANIDE™ adjuvants (W/O, W/O/W, O/W, IMS and Gel) (SEPPIC). The adjuvant concentration in the final immunological composition or vaccine composition can range between 5% to 80% v/v.

In the case of immunological composition and/or vaccine based on a baculovirus/insect cell-expressed polypeptides, a dose may include, about 1 µg to about 2000 µg, about 50 µg to about 1000 µg, and from about 100 µg to about 500 µg of FMDV antigen, epitope or immunogen. The dose may include about $10^2$ to about $10^{20}$, about $10^3$ to about $10^{18}$, about $10^4$ to about $10^{16}$, about $10^5$ to about $10^{12}$ VLPs (viral like particles). In the case of immunological composition and/or vaccine based on a viral vector expressing FMDV antigens, a dose may include, about $10^3$ viral particles to about $10^{15}$ viral particles, about $10^3$ viral particles to about $10^{14}$ viral particles, about $10^3$ viral particles to about $10^{13}$ viral particles, about $10^3$ viral particles to about $10^{12}$ viral particles. The viral particles may be calculated based on any virus titration methods including, but not limited to, FFA (Focus Forming Assay) or FFU (Focus Forming Unit), $TCID_{50}$ (50% Tissue Culture Infective Dose), PFU (Plaque Forming Units), and $FAID_{50}$ (50% Fluorescent Antibody Infectious Dose). The dose volumes can be between about 0.1 and about 10 ml, between about 0.2 and about 5 ml.

The disclosure will now be further described by way of the following non-limiting examples.

EXAMPLES

Construction of DNA inserts, plasmids and recombinant viral vectors was carried out using the standard molecular biology techniques described by J. Sambrook et al. (Molecular Cloning: A Laboratory Manual, 4th edition, Cold Spring Harbor Laboratory, Cold Spring Harbor, N.Y., 2014).

Example 1 Construction of Recombinant Human Adenovirus 5 Vectored FMDV Antigens

Example 1.2 Construction of Recombinant Human Adenovirus 5 Vectored FMDV Chimeric A24-A12 Antigen The Human Adenovirus C, serotype 5 (Ad5) vector (adenovirus vector) with deletions in the E1, E3, and E4 regions of the genome (GV11 backbone, see U.S. Pat. No. 8,323,663) was used to construct the recombinant FMDV vaccine expressing chimeric FMDV protein. The chimeric FMDV protein contains structural capsid gene of FMDV serotype A24 (A24 P1) and nonstructural genes A24 (2A-partial 2B), nonstructural partial 3B gene and the protease gene of FMDV serotype A12 (partial 3B-C3) (SEQ ID NO:2).

The chimeric polynucleotide encoding FMDV A24 (P1-2A-partial 2B)-A12 (partial 3B-3C) was introduced into the shuttle plasmid (see FIGS. 2 and 3). After co-transformation of the linearized GV11 backbone plasmid (which carries a kanamycin resistance gene) and the linearized shuttle plasmid containing the chimeric FMDV polynucleotide into BJDE3 E. coli cells, kanamycin-resistant clones of E. coli were selected. Clones bearing recombinant plasmids were confirmed by RFLP. A single clone was selected, the plasmid linearized and transfected into M2A cells. The lysate from the M2Acell transfection was serially passaged to produce high-titered stock of recombinant adenovirus vectored chimeric FMDV vaccine.

The donor gene insertion site is between the CMV promoter and SV40 PolyA of an Ad5 E1 expression cassette, and the expression cassette is inserted into the BBA at the E1 region The A24-A12 expression cassette, located at the E1 region deletion junction, reads right-to-left with respect to the viral genome RNA transcription. There are no known regulatory signals in the flanking nucleotide sequence of the insertion cassette. The CMV enhancer/promoter controls the initiation of transcription. Within this sequence are the viral enhancer CAAT box, TATA box, transcription start site, and 5' splice site sequences.

The CMV sequences are followed by an artificial untranslated region (UTR) containing a splice donor sequence. The open reading frame of the gene to be expressed follows the 3' splice site sequences and the Simian Virus 40 (SV40) early polyadenylation signal is positioned 3' of the open reading frame to terminate transcription.

Primer pairs were designed for the RBA Genetic Structural Identity (GSI) assay. The GSI assay uses PCR to identify the backbone biological agent and the expression cassette. The GSI blot (see FIG. 4) showed the correct backbone and A24-A12 FMDV expression cassette. Sequence analysis of the A24-A12 expression cassette also confirmed the nucleotide sequence identity between the shuttle plasmid and the DNA extracted from the recombinant adenovirus vectored chimeric A24-A12 FMDV vaccine.

The recombinant adenovirus vectored chimeric A24-A12 FMDV vaccine was confirmed to express A24 protein in vitro in 293 cells by a western blot assay, yielding a reactive protein that migrated to the position of approximately 28 KDa (see FIG. 5). The antibody used for detection in the Western Blot assay is a monoclonal antibody. The molecular weight of the A24 protein expressed from the recombinant adenovirus vectored chimeric A24-A12 FMDV vaccine was indistinguishable from that observed following transfection of the positive control shuttle plasmid into 293 cells (see FIG. 5).

Example 1.2 Construction of Recombinant Human Adenovirus 5 Vectored FMDV O1M Antigen The Human Adenovirus C, serotype 5 (Ad5) vector (adenovirus vector) with deletions in the E1, E3, and E4 regions of the genome (GV11 backbone, see U.S. Pat. No. 8,323,663) was used to construct the recombinant FMDV vaccine expressing FMDV protein. The FMDV protein contains structural capsid P1 (VP4-VP2-VP3-VP1) and the nonstructural proteins 2ABC and 3ABC including the full-length protease 3C (SEQ ID NO: 4) from FMDV O1/Man/87 strain.

The synthetic polynucleotide (SEQ ID NO: 3) encoding FMDV O1M P1 (VP4-VP2-VP3-VP1-2ABC'3A'BC) was introduced into the shuttle plasmid (see FIG. 6). The recombinant adenovirus vectored O1M FMDV vaccine was constructed following the procedure as described in Example 1.2.

The O1M87 FMDV expression cassette, located at the E1 region deletion junction, reads right-to left with respect to the viral genome RNA transcription. There are no known regulatory signals in the flanking nucleotide sequence of the insertion cassette. The CMV enhancer/promoter controls the initiation of transcription. Within this sequence are the viral enhancer CAAT box, TATA box, transcription start site, and 5' splice site sequences.

The CMV sequences are followed by an artificial untranslated region (UTR) containing a splice donor sequence. The open reading frame of the gene to be expressed follows the 3' splice site sequences and the Simian Virus 40 (SV40)

early polyadenylation signal is positioned 3' of the open reading frame to terminate transcription.

The GSI blot showed the correct backbone and O1M87 FMDV expression cassette. Sequence analysis of the O1M87 FMDV expression cassette also confirmed the nucleotide sequence identity between the shuttle plasmid and the DNA extracted from the recombinant adenovirus vectored O1M87 FMDV vaccine. The recombinant adenovirus vectored O1M87 FMDV vaccine was confirmed to express O1M87 protein in vitro in 293 cells by a western blot assay.

Example 1.3 Construction of Recombinant Human Adenovirus 5 Vectored FMDV Irn Antigen The Human Adenovirus C, serotype 5 (Ad5) vector (adenovirus vector) with deletions in the E1, E3, and E4 regions of the genome (GV11 backbone, see U.S. Pat. No. 8,323,663) was used to construct the recombinant FMDV vaccine expressing FMDV protein. The synthetic FMDV capsid coding sequence of P1 and nonstructural genes 2A, 2B, partial 2C (2C'), partial 3A (3A'), 3B and the protease coding sequence of 3C of FMDV serotype A/Irn/05 was introduced into a shuttle plasmid (see FIG. 7). The recombinant adenovirus vectored Irn FMDV vaccine was constructed following the procedure as described in Example 1.2.

The Irn FMDV expression cassette, located at the E1 region deletion junction, reads right-to left with respect to the viral genome RNA transcription. There are no known regulatory signals in the flanking nucleotide sequence of the insertion cassette. The CMV enhancer/promoter controls the initiation of transcription. Within this sequence is the viral enhancer CAAT box, TATA box, transcription start site, and 5' splice site sequences.

The CMV sequences are followed by an artificial untranslated region (UTR) containing a splice donor sequence. The open reading frame of the gene to be expressed follows the 3' splice site sequences and the Simian Virus 40 (SV40) early polyadenylation signal is positioned 3' of the open reading frame to terminate transcription.

The recombinant adenovirus vectored Irn FMDV vaccine was identified using a PCR-based Genetic Structural Identity (GSI) assay and confirmed using protein expression by western blot technique.

Example 1.4 Construction of Recombinant Human Adenovirus 5 Vectored FMDV Asia Antigen The Human Adenovirus C, serotype 5 (Ad5) vector (adenovirus vector) with deletions in the E1, E3, and E4 regions of the genome (GV11 backbone, see U.S. Pat. No. 8,323,663) was used to construct the recombinant FMDV vaccine expressing FMDV protein. The synthetic FMDV capsid coding sequence of P1 and nonstructural genes 2A, 2B, partial 2C (2C'), partial 3A (3A'), 3B and the protease coding sequence of 3C from FMDV strain Asia/Leb/89 was introduced into a shuttle plasmid (see FIG. 8). The recombinant adenovirus vectored Asia FMDV vaccine was constructed following the procedure as described in Example 1.2.

The Asia FMDV expression cassette, located at the E1 region deletion junction, reads right-to left with respect to the viral genome RNA transcription. There are no known regulatory signals in the flanking nucleotide sequence of the insertion cassette. The CMV enhancer/promoter controls the initiation of transcription. Within this sequence are the viral enhancer CAAT box, TATA box, transcription start site, and 5' splice site sequences.

The CMV sequences are followed by an artificial untranslated region (UTR) containing a splice donor sequence. The open reading frame of the gene to be expressed follows the 3' splice site sequences and the Simian Virus 40 (SV40) early polyadenylation signal is positioned 3' of the open reading frame to terminate transcription.

The recombinant adenovirus vectored Asia FMDV vaccine was confirmed to express Asia protein in vitro in 293 cells by a western blot assay, yielding a reactive protein that migrated to the position of approximately 38 kDa. The antibody used for detection in the Western Blot assay is the FMD VP2 polyclonal. The molecular weight of the AsiaSS.2B protein expressed was indistinguishable from that observed following transfection of the positive control plasmid into 293 cells.

Example 2 Challenge Study in Cattles and Pigs

Cattles and pigs were vaccinated with the A24-A12 FMDV vaccine or O1M87 FMDV vaccine once at Day 0 via IM and challenged at day 14 by many FMDV serotypes, such as A24, A12, O1, Asia, Irn, and Iraq strains.

FIG. 9 shows the protection of O1 FMDV vaccine in animals against FMDV challenge at three different doses and control. In this dose titration study, the recombinant adeno-vectored O1M FMDV vaccine was evaluated for the ability to confer protection against FMD generalized disease (pedal lesions) following direct, IDL homologous challenge at 14 days post-vaccination (dpv). Healthy 6 month old female Holstein cattle were randomized to one of four treatment groups. Control, naïve cattle (T01; n=4) were immunized intramuscularly with a single, 2 mL dose of final formulation buffer (FFB). Cattle in T02-T04 (n=7/group) were vaccinated with decreasing doses [Anti-adenovirus hexon focus forming units (FFU) or focus forming assay (FFA); $\log_{10}$] of active ingredient prepared from master seed virus passage 2 (MSV+2) formulated in ENABL™ C1 adjuvant. T02-T04 received $2.38\times10^5$, $5.94\times10^4$ FFU or $1.49\times10^4$ FFU total dose, respectively. At 2 weeks post-vaccination (day of challenge), 100% of T02 and T03 vaccinates had FMDV O1 Manisa serum virus neutralizing (SVN) titers, versus 43% in the lowest vaccine dose treatment group (T04). Following intradermal lingual challenge with $1\times10^4$ bovine infectious dose units 50% ($BID_{50}$) of FMDV O1 Manisa, 100% of T01 control, naive cattle exhibited generalized disease (pedal lesions). In contrast, the level of protection against generalized disease in vaccinated groups ranged from 86% (T04) to 100% (T02 and T03). All four control cattle (T01) were FMDV positive in plasma collected on 1-3 days post-challenge (dpc), whereas none of the twenty-one vaccinates had detectable plasma viremia on 1-5 dpc. In T01, 88% of the nasal samples collected 2-5 dpc were virus positive, compared to 25% (T03), 27% (T02) and 36% (T04) of the 2-5 dpc tested samples. FIG. 10 shows the serology of O1 FMDV vaccine at three doses and control.

These results demonstrate that the a recombinant adenovector O1M FMDV vaccine active ingredient formulated in ENABL C1 adjuvant is highly immunogenic and efficacious against IDL, homologous FMDV challenge in cattle, and provides data on the estimated minimum protective dose.

Both A24-A12 and O1M87 vaccines were tested to be safe in calves and mice.

Example 3 Adjuvant Serology Immunogenicity and Corresponding Viricidal/Stability Study Adjuvanting a vaccine can reduce the minimum protective dose (MPD) and result in a more effective vaccine. A reduced MPD may be balanced by the adjuvant cost and supply security. However, some adjuvants can reduce the vaccine effectiveness. The adjuvant may push the immune system towards an undesirable response or the adjuvant may be detrimental to the immunizing agent (lack of stability for example).

The objective of the study was to assess the adjuvant serology efficacy. An efficacy serology study was conducted in cattle, and in parallel a virucidal/stability study was performed to determine if any of the five adjuvants have detrimental effects on the adenovirus FMDV vaccines. Each dose consists of 200 μl of final AI (Active Ingredient) per dose at a 2 ml dose with each of the adjuvants. The adjuvants are polyacrylic acid, LF2 emulsion, LR6 emulsion, CARBIGEN™ M and ENABL® C1 (see Table 1.1 below).

TABLE 1.1

Preparation of adenovirus FMDV vaccines

| Group | Adjuvant | Vaccine formulation |
|---|---|---|
| G1 | No adjuvant | FMDV vaccine ($10^{5.7}$ per ml) + FFB (final formulation buffer) (50% v/v) |
| G2 | Polyacrylic acid | FMDV vaccine ($10^{5.7}$ per ml) + polyacrylic acid polymer (4 mg/2 ml dose) |
| G3 | LF2 emulsion | FMDV vaccine ($10^{5.7}$ per ml) + TS6* at 20% v/v of final serial |
| G4 | LR6 emulsion | FMDV vaccine ($10^{5.7}$ per ml) + LR4** at 25% v/v final serial |
| G5 | CARBIGEN™ M | FMDV vaccine ($10^{5.7}$ per ml) + CARBIGEN™ M to 10% v/v final serial |
| G6 | ENABL® C1 | FMDV vaccine ($10^{5.7}$ per ml) + ENABL® C1 (20% in final serial) |

TS6*: TS6 adjuvant/emulsion as described in U.S. Pat. No. 7,608,279 and U.S. Pat. No. 7,371,395
LR4**: LR4 adjuvant/emulsion as described in U.S. Pat. No. 7,691,368
CARBIGEN™: a carbomer-based (Carbopol 934P) adjuvant suspension, product of MVP Laboratories, Inc.
ENABL® C1: adjuvant product for cattle purchased commercially from VaxLiant

TABLE 1.2

TS6 emulsion (premulsion described in U.S. Pat. No. 7,608,279 and U.S. Pat. No. 7,371,395)

| Oily phase (120 ml) | |
|---|---|
| Sorbitan monooleate (SPAN 80®) | 1.8% w/v |
| Sorbitan trioleate (20 OE) (TWEEN 85®) | 10.2% w/v |
| Paraffin oil (MARCOL 82®) | 88% v/v |

TABLE 1.2-continued

TS6 emulsion (premulsion described in U.S. Pat. No. 7,608,279 and U.S. Pat. No. 7,371,395)

| Aqueous phase (120 ml) | |
|---|---|
| 20% (w/v) solution of sorbitan monooleate (20 OE) (TWEEN 80®) | 11.25% w/v |
| Phosphate disodic and monopotassic 0.02M isotonic buffer (pH 7.8) | 85.75% v/v |
| Sodium mercurothiolate (Thionersal®) 1% in water | 1.5% v/v |

TABLE 1.3

LR4 emulsion (premulsion described in U.S. Pat. No. 7,691,368)

| Oily phase (72 ml) | |
|---|---|
| Oleth-2 (BRIJ® 92) | 1.8% w/v |
| Oleth-5 (VOLPO® N5) | 8.2% w/v |
| Paraffin oil (MARCOL 82®) | 87.5% v/v |
| Preservative | 2.5% v/v |
| Aqueous phase (108 ml) | |
| Poloxamer 407 (LUTROL® F127) | 0.58% w/v |
| Isotonic buffer containing disodium and monopotassium phosphate 0.02M (pH 7.8) | Q.S. to 100.0% v/v |

Vaccines were stored at 4° C. and 25° C. and tested over time. The viruses in each vaccine were titrated in accordance with the standard focus forming assay titration assay wherein the amount of virus detected is read by specific anti-adenovirus antibodies on the cell monolayer. The respective titers were compared. Data from the first 3 months is presented below, in Table 2 and in FIGS. 11 (25° C.) and 12 (4° C.). At 4° C., most antigens or viruses present in the formulated vaccines are stable out to 3 months. At 25° C., antigens or viruses formulated with adjuvants polyacrylic acid, LF2 and Carbigen M are relatively stable out to 7 weeks. The stability of these three formulations showed a slight decrease at 25° C. at 3-months point. However, this drop is less when the recombinant viruses is combined with adjuvant confirming the protective effect of adjuvant. The antigens or viruses formulated with adjuvant LR6 experienced some adjuvant assay interference as evidenced from the below detection level at both 4° C. and 25° C. However, the formulation adjuvanted with LR6 generated specific virus titer at 3 months and is stable at 25° C.

TABLE 2

Viricidal and stability study of five adjuvants up to 3 months

| Adjuvant | T = 0 | T = 24 hr | T = 1 week | T = 2 week | T = 4 week | T = 7 week | T = 3 months |
|---|---|---|---|---|---|---|---|
| G1-4° C. | 6.94 | 6.61 | 6.88 | 6.90 | 6.89 | 6.80 | 7.21 |
| G1-25° C. | 7.10 | 6.70 | 6.76 | 6.34 | 5.59 | 4.24 | Below detection |
| G2-4° C. | 6.97 | 6.51 | 7.04 | 6.96 | 6.97 | 6.90 | 7.07 |
| G2-25° C. | 6.91 | 6.40 | 6.94 | 6.93 | 6.69 | 6.56 | 5.85 |
| G3-4° C. | 6.68 | 6.25 | 6.74 | 6.80 | 6.74 | 6.93 | 6.92 |
| G3-25° C. | 6.42 | 6.40 | 6.71 | 6.69 | 6.67 | 6.63 | 5.85 |
| G4-4° C. | 6.51 | Below Detection* | 6.69 | 5.36 | Below Detection* | Below Detection* | 6.78 |
| G4-25° C. | 6.52 | Below Detection* | 6.69 | 5.44 | Below Detection* | Below Detection* | 6.21 |
| G5-4° C. | 6.82 | 6.81 | 6.91 | 6.80 | 6.96 | 7.17 | 7.13 |
| G5-25° C. | 6.87 | 6.83 | 6.92 | 6.51 | 6.61 | 6.42 | 5.85 |
| G6-4° C. | 6.84 | 6.79 | 6.95 | 6.77 | 6.73 | 7.11 | 7.16 |
| G6-25° C. | 6.84 | 6.84 | 6.81 | 6.72 | Below detection | Below detection | Below detection |

Below Detection*: adjuvant assay interference

The corresponding serology study was conducted in cattle. Each group contained 10 animals per experimental group (5 in control) and was administered one 2 ml dose at day zero followed by a boost at day 21. Blood samples were taken at several timepoints throughout the study and the serum samples were analyzed. Serology by Virus Neutralizing Titer was conducted. The initial data indicated serological responses at day 14 post first vaccination in several groups. Taken together, the data indicates that adenovirus-vectored FMD vaccines formulated in certain adjuvants may provide opportunities for thermostability improvements and ability to handle temperature excursions. When combined with these initial data, the immunological response is either maintained or potentially improved.

Example 4 Serology Immunogenicity of Two-Dose Vaccination with Multiple Recombinant Human Adenovirus Vectored FMDV O1M Antigen in Cattle The goal of the study is to assess the serological antibody response in cattle following the administration of Adeno Vectored FMDV O1Manisa formulated with and without different adjuvants.

Fifty-five conventionally reared calves (approximately 5 months of age) were each randomized to one of six treatment groups as presented in Table 4 below.

TABLE 4

| Group | Vaccine | Adjuvant | Route of Administration | Frequencey of Administration | No. of animals |
|---|---|---|---|---|---|
| 1 | Adt.O1/Manisa | ENABL ® C1 | IM | Twice 21; days apart | 10 |
| 2 | Adt.O1/Manisa | LF | IM | Twice 21; days apart | 10 |
| 3 | Adt.O1/Manisa | Polyacrylic acid | IM | Twice 21; days apart | 10 |
| 4 | Adt.O1/Manisa | Carbigen M | IM | Twice 21; days apart | 10 |
| 5 | Adt.O1/Manisa | None | IM | Twice 21; days apart | 10 |
| 6 | FFB Placebo | None | IM | Twice 21; days apart | 5 |

All calves except those from Group 6 (sentinels) were vaccinated with an Adenovirus vectored O1/Manisa construct with (Groups 1-4) or without an adjuvant (Groups 5), twice at a 21-day interval with 2 ml of the test vaccine. All injections were given via the intramuscular route (IM) over the shoulder alternately on the right and left sides. Table 4 above contains a summary of the treatment for each group.

Calves were intermittently observed for at least 1 hour following each vaccination for clinical signs of acute systemic adverse events. Blood samples were collected from all cattle on Days −1 (prior to vaccination), 7, 15, 21 (prior to vaccination), 28, and 35. Serum samples from all cattle were tested for FMDV antibodies by Serum Virus Neutralization (SVN). In addition, antibody responses to Adenovirus (SAV) were determined in all animals from all groups in samples collected on Day −1 and 35. The results for SVN and SAV were reported in $Log_{10}$ and a value $\leq 0.6$ $Log_{10}$ was considered negative for serum antibody.

Post-vaccination safety assessments included rectal temperature, visual inspection and palpation of injection sites for at least 3 days following each vaccination. Cows with local injection site adverse events were observed intermittently until resolution of the abnormality. The study was terminated on D35 after the final blood collection.

Results of FMDV serological response using FMDV antibodies by Serum Virus Neutralization (SVN) $Log_{10}$ are described below.

Figure 13:
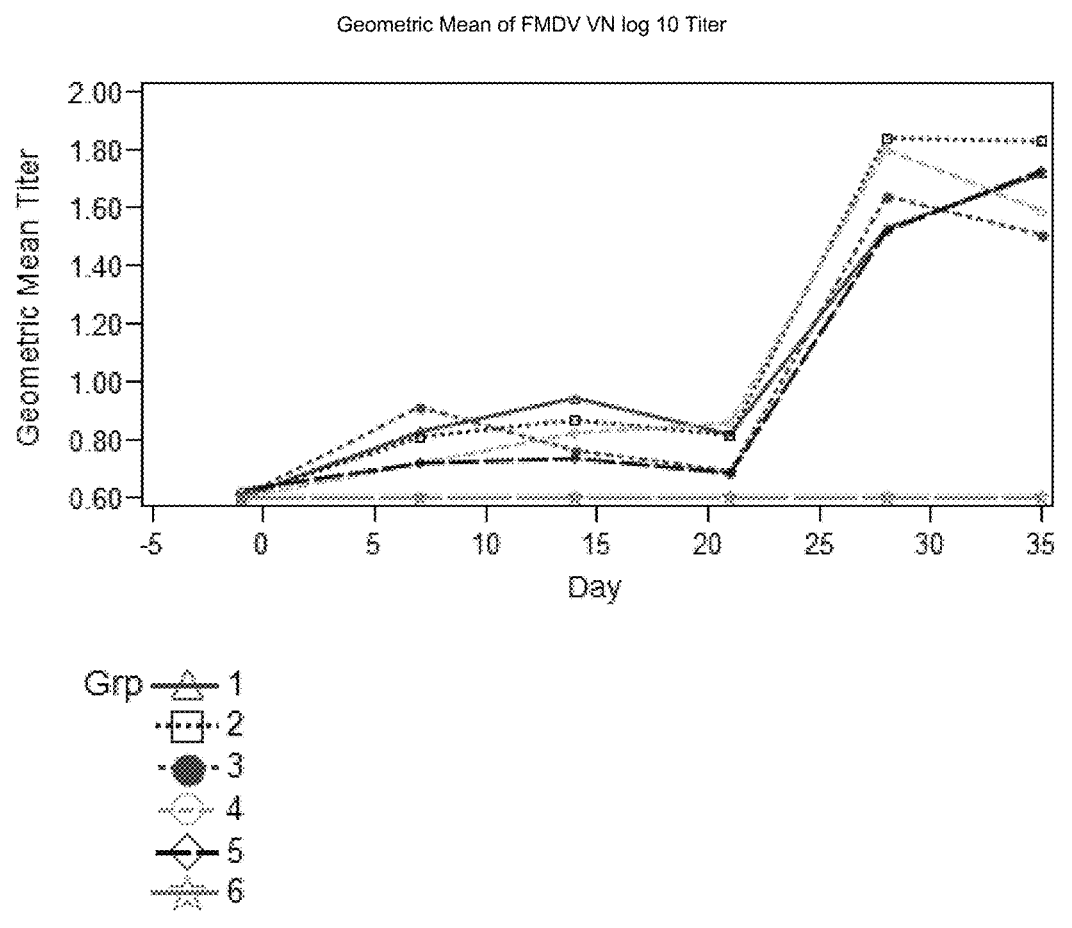

All calves from all Groups tested negative for FMDV antibodies prior to the start of the study. All sentinels were negative for FMDV antibodies throughout the study. Seroconversion following vaccination was defined as an increase $Log_{10}$ titer>0.9. By Day 14 (2 weeks following the 1st vaccination), 5/10 calves (50%) in the ENABL® C1 (Group 1) had seroconverted. Those in the remaining vaccinated groups (2-5) had between 20-40% of the calves seroconvert. In addition, the mean antibody titer per group was slightly higher in group 1 (ENABL® C1) followed by Groups 2 (LF) and 3 (Polyacrylic acid) (FIG. 13).

By Day 35 (2 weeks following the 2nd vaccination), all vaccinated animals (Groups 1 [ENABL®], group 2 [LF] and group 5 [no adjuvant]) had seroconverted followed by ninety and eighty percent of those in groups 3 (Polyacrylic acid) and 4 (Carbigen M) respectively. Animals vaccinated with the LF, adjuvant, followed by those vaccinated without adjuvant (Group 5) and by those vaccinated with the ENABL® C1 (Group 1) adjuvant had a higher antibody response following a two-dose vaccination regime (see FIG. 13).

Results of FMDV serological response using Adenovirus antibodies by Serum Virus Neutralization (SVN) $Log_{10}$ are described below.

Figure 14:
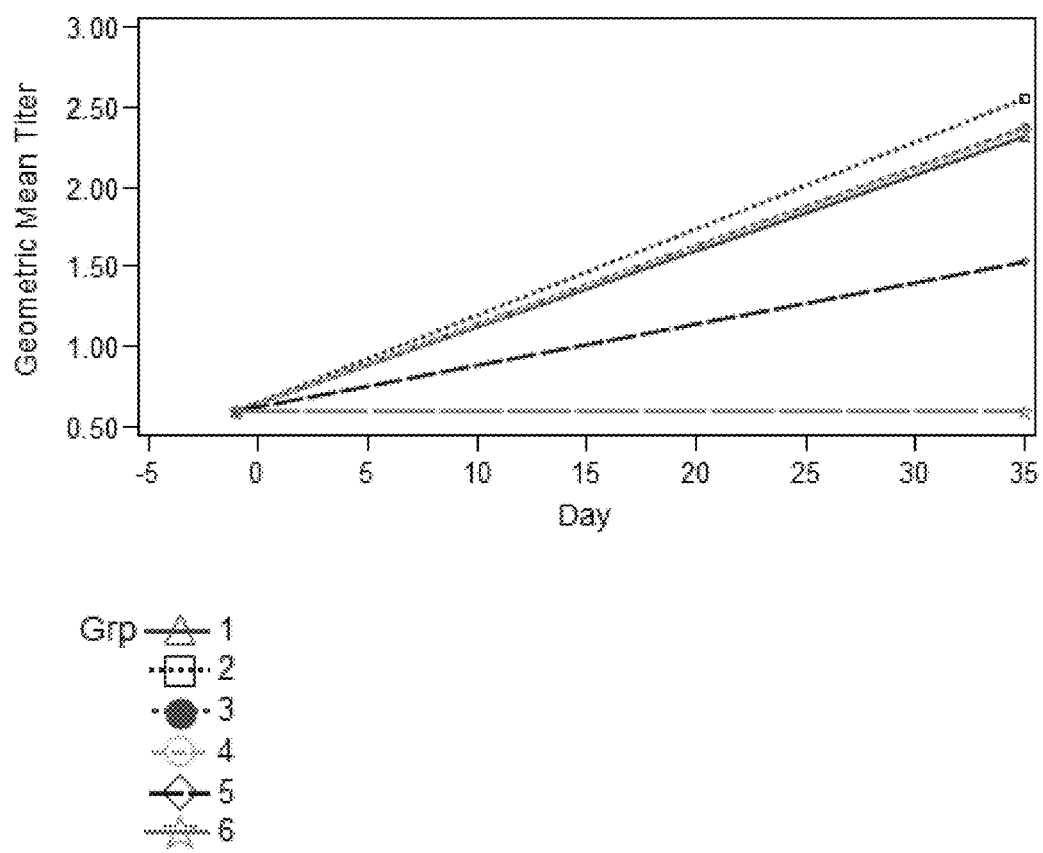
FIG. 14 depicts the geometic mean of SAV titer.

All sentinels and vaccinated calves were negative to Adenovirus by SN antibody titers on Day −1 ($\leq 0.6$ $Log_{10}$). By day 35, all but one of the vaccinated calves (ID: 134; Group 5) seroconverted with an overall higher geo mean titer by group in those vaccinated with a vaccine containing adjuvant (Groups 1-4) (see FIG. 14).

The results indicated serological responses at day 14 post first vaccination in several groups. Two weeks after the second vaccination the higher antibody response was seen in vaccinated calves with the LF adjuvant followed by those vaccinated without adjuvant and with the Enable C1 adjuvant.

The results suggest that the antibody response following a single vaccination regardless of the presence or absence of adjuvant is small. However, using a two vaccination (prime-boost) regimen the antibody response is overall higher. There were no systemic adverse events observed when the vaccine construct was administered twice (3 weeks apart) intramuscularly.

Example 5 Serology Assessment of FMDV Vaccines Following Vaccination in Pigs

The goal of the study is to assess the antibody response in piglets following the administration of monovalent vaccine formulations containing Adeno 5 Vectored FMDV O1 Manisa) and/or FMDV baculovirus-expressed O1 Manisa recombinant Virus Like Particle (VLP).

Twenty conventionally reared piglets (approximately 5 weeks of age) were randomized to two treatment groups, each containing 10 piglets. The group composition is presented in Table 5 below.

TABLE 5

| Group | Vaccines | dose per piglet; Adenovirus constructs (FAID$_{50}$/ 2 ml (log$_{10}$) | Frequency | No. of Animals |
|---|---|---|---|---|
| 1 | Adenovirus O1M No adjuvant/ Bac O1M + Adjuvant TS6 | $10^8$ | Adenovirus X + 5 O1M (Day 0) and Bac O1M Adjuvant TS6 (Day 21) | 10 |
| 2 | Sentinel (N/A) | N/A | N/A | 10 |

Piglets in group 1 were vaccinated with 2 ml of the vaccine. All injections were given via the intramuscular route (IM) over the shoulder alternately on the right and left sides. Piglets were observed prior to each vaccination for their overall health condition. Blood samples were collected from all piglets on Days 0 (prior to vaccination), 7, 14, 21 (prior to vaccination), 28 and 35. Day 35 serum samples from all piglets were tested for FMDV antibodies by Serum Virus Neutralization (SVN). Samples from those piglets in group 1 were subject to SVN assay on all collection days since they had an overall higher antibody response following on Day 35. The results were reported in Log$_{10}$ and a value ≤0.75 Log$_{10}$ was considered negative for serum antibody. Post-vaccination safety assessments included rectal temperature, visual inspection and palpation of injection sites for 3 days following each vaccination.

Results of FMDV serological response using FMDV antibodies by Serum Virus Neutralization (SVN) Log$_{10}$ are described below.

Figure 15:
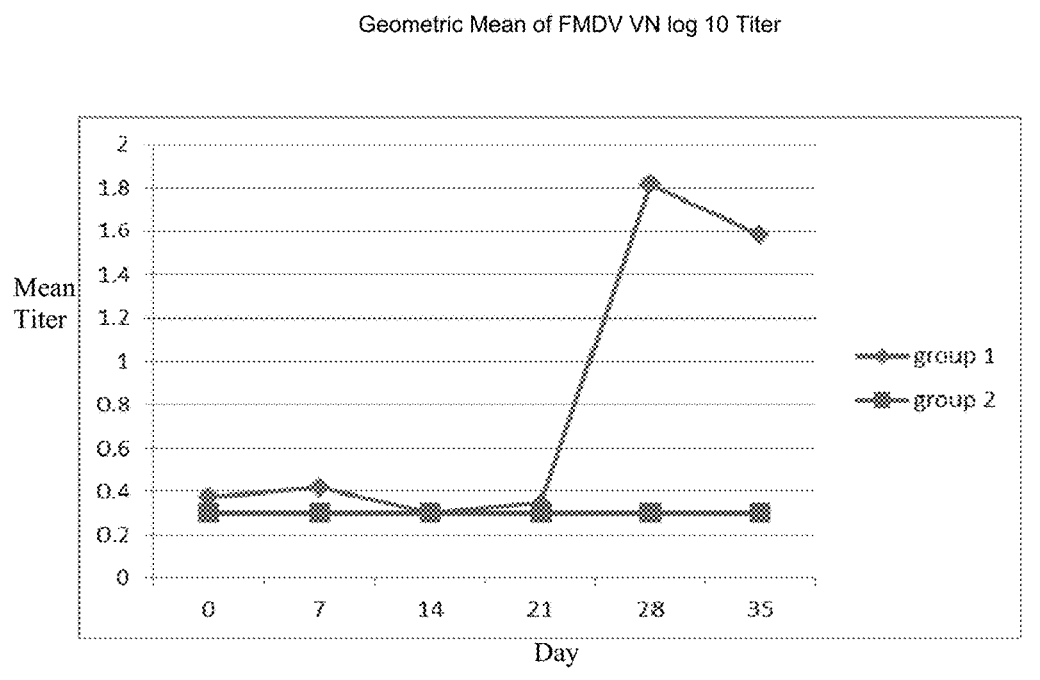

All sentinels were negative for FMDV antibodies prior to and at the end of the study. By Day 28 (1 week following the 2nd vaccination), all piglets from Group 1 seroconverted (titers ≥1.20 log$_{10}$) (see FIG. 15). No systemic and/or local adverse events attributable to vaccination were observed. The results clearly showed that even though vaccinated group had a small antibody response following the first vaccination, the antibody response following the second (prime-boost) vaccination was high by the end of the study.

Example 6 Route of Administration

The goal of the study is to evaluate the serological response of two-dose vaccination in cattle or pigs when two recombinant Adenovirus vectored FMDV vaccines, one recombinant Adenovirus vectored FMDV vaccine and one baculovirus-expressed recombinant FMDV Virus like particle (VLP) vaccine, or two FMDV VLP vaccines are used, and when different routes of administration (transdermal, subcutaneous, or intradermal route of administration) are used. The study is also designed to address interference issue when multiple vaccines are administered.

The adjuvants are polyacrylic acid, LF2 emulsion, LR6 emulsion, CARBIGEN™ M and ENABL® C1. The treatment groups are represented in Table 6 below.

Table 6

| Group | Vaccines | Administration route | Frequency of administration |
|---|---|---|---|
| 1 | Adeno FMDV | IM or IM/TD or IM/SQ | Twice, 21 days apart |
| 2 | Adeno FMDV | TD or TD/IM or TD/SQ | Twice, 21 days apart |
| 3 | Adeno FMDV | SQ or SQ/TD or SQ/IM | Twice, 21 days apart |
| 4 | Baculo FMDV VLP | IM or IM/TD or IM/SQ | Twice, 21 days apart |
| 5 | Baculo FMDV VLP | TD or TD/IM or TD/SQ | Twice, 21 days apart |
| 6 | Baculo FMDV VLP | SQ or SQ/TD or SQ/IM | Twice, 21 days apart |
| 7 | Adeno FMDV/Beculo FMDV VLP | IM or IM/TD or IM/SQ | Twice, 21 days apart |
| 8 | Adeno FMDV/Beculo FMDV VLP | TD or TD/IM or TD/SQ | Twice, 21 days apart |
| 9 | Adeno FMDV/Beculo FMDV VLP | SQ or SQ/TD or SQ/IM | Twice, 21 days apart |

Calves are intermittently observed for at least 1 hour following each vaccination for clinical signs of acute systemic adverse events. Blood samples are collected from all cattle on Days −1 (prior to vaccination), 7, 15, 21 (prior to vaccination), 28, and 35. Serum samples from all cattle were tested for FMDV antibodies by Serum Virus Neutralization (SVN). In addition, antibody responses to Adenovirus (SAV) are determined in all animals from all groups in samples collected on Day −1 and 35.

Post-vaccination safety assessments include rectal temperature, visual inspection and palpation of injection sites for at least 3 days following each vaccination. Cows with local injection site adverse events are observed intermittently until resolution of the abnormality.

The results show a prime-boost affect for all groups but the prime-boost effect is greater in animals that received a prime with the adenovirus vaccine followed by a boost with the baculovirus-FMD construct. Furthermore, the route of administration has an impact on serological response and protection, as well as duration of immunity. Specific routes of administration and/or specific combination of administration routes TD, IM and SQ appear to exacerabet the immune response, further appliify protection, overcome interference, and protect Maternally Derived Antibody-positive (MDA-positive) animals.

Example 7 Efficacy in Swine

Pigs are vaccinated against FMDV (against several setotypes) twice with 21-days apart in a prime-boost regimen that looked at a heterologous prime-boost protocol (adeno prime followed by baculo boost) as well as homologous prime boost (adeno-adeno; baculo-baculo), and challenged 14 dpv by many FMDV serotypes, such as A24, A12, O1, Asia, Irn, and Iraq strains.

In the dose titration study, the recombinant adeno-vectored FMDV vaccine is evaluated for the ability to confer protection against FMD generalized disease (pedal lesions) following homologous and heterologous challenges at 14 days post-vaccination (dpv). The procedure described in Example 2 is used in this study to determine the minimum protective dose in the prime-boost administration regimen.

The results demonstrate that the recombinant adenovector FMDV vaccine used in primer-boost protocol is highly immunogenic and efficacious against homologous and heterologous FMDV challenges in pigs, overcomes interference and protects Maternally Derived Antibody-positive (MDA-positive) animals.

Example 8 Efficacy in Bovine

Cattles are vaccinated first with a recombinant Adenovirus vectored FMDV vaccine and bossted with a conventional killed FMD vaccine or a baculovirus-expressed FMDV VLP vaccine 21-day apart and challenged at day 14 post second vaccination by many FMDV serotypes, such as A24, A12, O1, Asia, Irn, and Iraq strains.

In the dose titration study, the recombinant adeno-vectored FMDV vaccine is evaluated for the ability to confer protection against FMD generalized disease (pedal lesions) following direct homologous and heterologous challenges at 14 days post-vaccination (dpv). The procedure described in Example 2 is used in this study to determine the minimum protective dose in the prime-boost administration regimen.

The results demonstrate that the prime-boost administration regimen is highly immunogenic and efficacious against homologous and heterologous FMDV challenges in cattle, and provides protection in animals against FMDV infection, overcome interference, and protects Maternally Derived Antibody-positive (MDA-positive) animals.

Having thus described in detail embodiments of the present disclosure, it is to be understood that the disclosure defined by the above examples is not to be limited to particular details set forth in the above description as many apparent variations thereof are possible without departing from the spirit or scope of the present disclosure.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

What we claim is:

1. A composition or vaccine comprising a recombinant viral vector that, when expressed, expresses a foot and mouth Disease Virus (FMDV) antigen comprising a polypeptide sequence selected from any one of SEQ ID NOS: 2, 4, 6, and 8.

2. The composition or vaccine of claim 1, wherein the viral vector is an adenovirus.

3. The composition or vaccine of claim 1, wherein the viral vector expresses structural and nonstructural FMDV proteins.

4. The composition or vaccine of claim 1, wherein the viral vector comprises a polynucleotide sequence selected from any one of SEQ ID NOS: 1, 3, 5, and 7.

5. The composition or vaccine of claim 1, further comprising a pharmaceutically or veterinarily acceptable carrier, excipient, adjuvant, or vehicle.

6. The composition or vaccine of claim 5, wherein the composition or vaccine is stable out to 3 months when stored at 4° C.

7. The composition or vaccine of claim 5, wherein the pharmaceutically or veterinarily acceptable carrier, excipient, adjuvant, or vehicle is selected from polyacrylic acid, LF2 emulsion, LR6 emulsion, TS6 emulsion, LR4 emulsion, carbomer, aluminum hydroxide, aluminum phosphate, saponin, CpG, water-in-oil emulsion, oil-in-water emulsion, carbomer-based adjuvant, and adjuvant composition comprising a lipophile, a polymer of acrylic or methacrylic acid, saline, cholesterol, a saponin, and sodium hydroxide.

8. A method of vaccinating an animal susceptible to FMDV infection or eliciting an immune response in the animal against FMDV comprising administering to the animal the vaccine according to claim 1.

9. A method of vaccinating all animal susceptible to FMDV infection or eliciting an immune response in the animal against FMDV comprising:
   administering to the animal a prime-vaccine; and then administering to the animal a boost-vaccine,
   wherein at least one of the prime-vaccine and the boost-vaccine is the vaccine according to claim 1.

10. The method of claim 9, wherein the prime-vaccine is the vaccine according to claim 1, wherein the boost-vaccine comprises an FMDV antigen, a recombinant viral vector that expresses, in vivo, an FMDV antigen, or both, and wherein the method protects the animal from FMDV and/or prevents FMDV disease progression in the animal.

11. The method of claim 9, wherein the prime-vaccine comprises an FMDV antigen, a recombinant viral vector that expresses, in vivo, an FMDV antigen, or both, wherein the boost-vaccine is the vaccine according to claim 1, and wherein the method protects the animal from FMDV and/or prevents FMDV disease progression in the animal.

12. The method of claim 8, wherein the method protects Maternally Derived Antibody-positive (MDA-positive) animals against FMDV infection.

\* \* \* \* \*